(12) United States Patent  
Wasielewski

(10) Patent No.: US 10,517,568 B2
(45) Date of Patent: Dec. 31, 2019

(54) 3-D ULTRASOUND IMAGING DEVICE AND METHODS

(71) Applicant: Joint Vue, LLC, Knoxville, TN (US)

(72) Inventor: Ray C. Wasielewski, New Albany, OH (US)

(73) Assignee: JointVue, LLC, Knoxville, TN (US)

( * ) Notice: Subject to any disclaimer, the term of this patent is extended or adjusted under 35 U.S.C. 154(b) by 954 days.

(21) Appl. No.: 14/178,726

(22) Filed: Feb. 12, 2014

(65) Prior Publication Data

US 2014/0163375 A1 Jun. 12, 2014

Related U.S. Application Data

(63) Continuation of application No. PCT/US2012/050590, filed on Aug. 13, 2012.
(Continued)

(51) Int. Cl.
*A61B 8/00* (2006.01)
*A61B 8/08* (2006.01)

(52) U.S. Cl.
CPC .......... *A61B 8/4477* (2013.01); *A61B 8/0875* (2013.01); *A61B 8/4227* (2013.01);
(Continued)

(58) Field of Classification Search
CPC ... A61B 8/4477; A61B 8/0875; A61B 8/4427; A61B 8/4494; A61B 8/483;
(Continued)

(56) References Cited

U.S. PATENT DOCUMENTS

| 3,881,164 A | 4/1975 | Kossoff |
| 4,476,873 A | 10/1984 | Sorenson et al. |

(Continued)

FOREIGN PATENT DOCUMENTS

| WO | 2000063719 A1 | 10/2000 |
| WO | 2010088696 A1 | 8/2010 |

(Continued)

OTHER PUBLICATIONS

Jurkonis et al., "Synthesis of Parametric Map from Raw Ultrasound B-Scan Data," 2009, Electronics and Electrical Engineering, ISSN 1329-1215, No. 6(94), pp. 109-112.*
(Continued)

*Primary Examiner* — Carolyn A Pehlke
(74) *Attorney, Agent, or Firm* — Dorton & Willis, LLP; Ryan Willis

(57) ABSTRACT

An ultrasound cover for use with an ultrasound imaging system, a method of examining a patient with ultrasound, and an ultrasound diagnostic system. The ultrasound cover includes a central layer configured to conform to a shape of a patient's body and a plurality of ultrasound sensors positioned within the central layer. The ultrasound cover is positioned on a patent to be examined and conformed to the shape of the patient's body. RF ultrasound signals are acquired from the plurality of sensors and a 3-D model of the patient created from extracted echoes. The cover may be used with a diagnostic system that includes a computer configured to compare ultrasound data to a orthopedic-specific dataset to locate bony boundaries.

10 Claims, 32 Drawing Sheets

Related U.S. Application Data

(60) Provisional application No. 61/522,942, filed on Aug. 12, 2011.

(52) U.S. Cl.
CPC .......... *A61B 8/4427* (2013.01); *A61B 8/4494* (2013.01); *A61B 8/483* (2013.01); *A61B 8/4236* (2013.01)

(58) Field of Classification Search
CPC ... A61B 8/4209; A61B 8/4227; A61B 8/4236; A61B 8/00; A61B 8/08; A61B 8/4483; A61B 8/46; A61B 8/4455; A61B 8/4272; A61B 8/4281; A61B 8/429
See application file for complete search history.

(56) References Cited

U.S. PATENT DOCUMENTS

| | | | |
|---|---|---|---|
| 5,394,875 A | 3/1995 | Lewis et al. | |
| 5,413,116 A | 5/1995 | Radke et al. | |
| 5,447,154 A | 9/1995 | Cinquin et al. | |
| 5,488,952 A | 2/1996 | Schoolman | |
| 5,771,310 A | 6/1998 | Vannah | |
| 5,806,521 A | 9/1998 | Morimoto et al. | |
| 6,106,463 A * | 8/2000 | Wilk .................. | A61B 5/742 600/437 |
| 6,106,464 A | 8/2000 | Bass et al. | |
| 6,120,453 A | 9/2000 | Sharp | |
| 6,190,320 B1 | 2/2001 | Lelong | |
| 6,213,958 B1 | 4/2001 | Winder | |
| 6,231,585 B1 | 5/2001 | Takahashi et al. | |
| 6,280,387 B1 | 8/2001 | Deforge et al. | |
| 6,517,484 B1 * | 2/2003 | Wilk .................. | A61B 8/00 600/437 |
| 6,537,233 B1 | 3/2003 | Rangayyan et al. | |
| 6,569,098 B2 | 5/2003 | Kawchuk | |
| 6,585,651 B2 | 7/2003 | Nolte et al. | |
| 7,454,242 B2 | 11/2008 | Fear et al. | |
| 7,660,623 B2 | 2/2010 | Hunter et al. | |
| 7,676,023 B2 | 3/2010 | Lang | |
| 7,678,052 B2 | 3/2010 | Torp et al. | |
| 7,684,846 B2 | 3/2010 | Johnson et al. | |
| 7,769,422 B2 | 8/2010 | DiSilvestro et al. | |
| 7,920,731 B2 | 4/2011 | Moreau-Gobard | |
| 7,949,386 B2 | 5/2011 | Buly et al. | |
| 8,089,417 B2 | 1/2012 | Popovic et al. | |
| 8,265,728 B2 | 9/2012 | MacMahon et al. | |
| 8,444,564 B2 | 5/2013 | Mahfouz et al. | |
| 2002/0082668 A1 | 6/2002 | Ingman | |
| 2005/0093859 A1 | 5/2005 | Sumanaweera et al. | |
| 2005/0165284 A1 | 7/2005 | Gefen | |
| 2005/0240098 A1 | 10/2005 | Zhong et al. | |
| 2006/0052727 A1 | 3/2006 | Palestrant | |
| 2007/0021738 A1 | 1/2007 | Nasser et al. | |
| 2007/0282200 A1 | 12/2007 | Johnson et al. | |
| 2007/0287900 A1 | 12/2007 | Breen et al. | |
| 2008/0009722 A1 | 1/2008 | Simopoulos et al. | |
| 2008/0094396 A1 | 4/2008 | Sabczynsdi et al. | |
| 2009/0015832 A1 | 1/2009 | Popovic et al. | |
| 2009/0018445 A1 | 1/2009 | Schers et al. | |
| 2009/0129652 A1 | 5/2009 | Zwim et al. | |
| 2009/0137907 A1 | 5/2009 | Takimoto et al. | |
| 2010/0022888 A1 | 1/2010 | George et al. | |
| 2010/0100011 A1 | 4/2010 | Roche | |
| 2010/0198067 A1 | 8/2010 | Mahfouz | |
| 2010/0234770 A1 | 9/2010 | Colombet et al. | |
| 2010/0256504 A1 | 10/2010 | Moreau-Gaudry et al. | |
| 2010/0277241 A1 | 11/2010 | Moldsvor | |
| 2011/0054313 A1 | 3/2011 | Kiyan | |
| 2011/0125016 A1 | 5/2011 | Lazebnik et al. | |
| 2011/0305379 A1 * | 12/2011 | Mahfouz .............. | A61F 2/3094 382/131 |
| 2011/0319755 A1 | 12/2011 | Stein et al. | |

FOREIGN PATENT DOCUMENTS

| | | |
|---|---|---|
| WO | 2014121244 A1 | 8/2014 |
| WO | 2014150780 A1 | 9/2014 |
| WO | 2014150961 A1 | 9/2014 |

OTHER PUBLICATIONS

United States Patent and Trademark Office, "International Preliminary Report on Patentability", in corresponding International Application No. PCT/US2010/022939, dated Aug. 2, 2011, 7 pp.

European Patent Office, "International Search Report and Written Opinion", in corresponding International Application No. PCT/US2011/046318, dated Nov. 11, 2011, 13 pp.

United States Patent and Trademark Office, International Search Report and Written Opinion, in corresponding International Application No. PCT/US2011/054952, dated Jan. 26, 2012, 9 pp.

United States Patent and Trademark Office, "International Search Report and Written Opinion", in corresponding International Application No. PCT/US2010/022939, dated Mar. 19, 2010, 4 pp.

United States Patent and Trademark Office, "Written Opinion of the International Preliminary Examining Authority", in corresponding International Application No. PCT/US2011/046318, dated Jul. 8, 2012, 6 pp.

United States Patent and Trademark Office, "International Search Report and Written Opinion", in corresponding International Application No. PCT/US2012/060261, dated Jan. 9, 2013, 10 pp.

United States Patent and Trademark Office, "Non-Final Office Action", in related U.S. Appl. No. 13/196,701, dated Apr. 10, 2013, 18 pp.

United States Patent and Trademark Office, "Final Office Action", in related U.S. Appl. No. 13/196,701, dated Dec. 19, 2013, 11 pp.

United States Patent and Trademark Office, "Non-Final Office Action", in related U.S. Appl. No. 12/364,267, dated Nov. 9, 2011, 15 pp.

United States Patent and Trademark Office, Final Office Action, in related U.S. Appl. No. 12/364,267, dated May 23, 2012, 18 pp.

European Patent Office, Written Opinion of the International Searching Authority, in corresponding International Application No. PCT/US2011/046318, 6 pp.

Mahfouz, Mohamed R. "Operating Room of the Future Orthopedic Perspective", Proceedings of the 2008 IEEE, CIBEC 2008, 9 pp.

United States Patent and Trademark Office, "International Search Report and Written Opinion", in corresponding International Application No. PCT/US2013/025131, dated Apr. 26, 2013, 8 pp.

United States Patent and Trademark Office, "International Search Report and Written Opinion", in corresponding International Application No. PCT/US2012/050590, dated Oct. 23, 2012, 8 pp.

Fleute, et al., Incorporating a Statistically Based Shape Model Into a System for Computer-Assisted Anterior Cruciate Ligament Surgery, Medical Image Analysis 1999 vol. 3, No. 3.

http://www.ultrasonix.com/wikisonix/index.php/Receiving_Ultrasound_Data.

European Patent Office, "Supplementary Search Report and Search Opinion", in published European Patent 2391971, dated Sep. 21, 2015, 10 pp.

European Patent Office, "Examination Report", in published European Patent 2391971, dated Apr. 19, 2018, 8 pp.

European Patent Office, "Supplementary Search Report and Search Opinion", in published European Patent 2741674, dated Mar. 9, 2015, 7 pp.

European Patent Office, "Supplementary Search Report and Search Opinion", in published European Patent 2765919, dated Jul. 3, 2015, 7 pp.

European Patent Office, "Supplementary Search Report and Search Opinion", in published European Patent 2950712, dated Aug. 18, 2016, 10 pp.

European Patent Office, "Supplementary Search Report and Search Opinion", in published European Patent 3213682, dated Jul. 17, 2017, 7 pp.

(56) References Cited

OTHER PUBLICATIONS

European Patent Office, "Supplementary Search Report and Search Opinion", in published European Patent 2967353, dated Oct. 6, 2016, 8 pp.

European Patent Office, "Examination Report", in published European Patent 2967353, dated Sep. 15, 2017, 4 pp.

European Patent Office, "Supplementary Search Report and Search Opinion", in published European Patent 2967440, dated Sep. 12, 2016, 7 pp.

European Patent Office, "Examination Report", in published European Patent 2967440, dated Dec. 11, 2018, 6 pp.

United States Patent and Trademark Office, "International Search Report and Written Opinion", in International Patent Application No. PCT/US2014/014526, dated Apr. 16, 2014, 9 pp.

United States Patent and Trademark Office, "International Preliminary Report on Patentability", in International Patent Application No. PCT/US2014/014526, dated Aug. 4, 2015, 7 pp.

United States Patent and Trademark Office, "International Search Report and Written Opinion", in International Patent Application No. PCT/US2014/024205, dated Sep. 10, 2014, 9 pp.

United States Patent and Trademark Office, "International Preliminary Report on Patentability", in International Patent Application No. PCT/US2014/024205, dated Sep. 15, 2015, 6 pp.

United States Patent and Trademark Office, "International Search Report and Written Opinion", in International Patent Application No. PCT/US2014/024652, dated Jul. 30, 2014, 15 pp.

United States Patent and Trademark Office, "International Preliminary Report on Patentability", in International Patent Application No. PCT/US2014/024652, dated Sep. 15, 2015, 10 pp.

European Patent Office, "Search Report and Search Opinion", in European Divisional Patent Application 19162658.9, dated Jul. 15, 2019, 13 pp.

Wei Dong et al, "A Low-Cost Motion Tracker and Its Error Analysis", 2008 IEEE International Conference on Robotics and Automation, The Half-Day Workshop on: Towards Autonomous Agriculture of Tomorrow, May 19, 2008, 6 pp.

Angelo Maria Sabatini, "Estimating Three-Dimensional Orientation of Human Body Parts by Inertial/Magnetic Sensing", Sensors, vol. 11, No. 2, Jan. 1, 2011, 37 pp.

* cited by examiner

3-D ULTRASOUND IMAGING DEVICE AND METHODS

CROSS-REFERENCE TO RELATED APPLICATIONS

This application is a continuation of and claims priority to International Application No. PCT/US2012/50590, entitled 3-D ULTRASOUND IMAGING DEVICE AND METHODS," filed Aug. 13, 2012 (pending), which claims the benefit of and priority to U.S. Provisional Patent Application Ser. No. 61/522,942, filed on Aug. 12, 2011, the disclosures of which are incorporated herein by reference in their entireties.

TECHNICAL FIELD

This invention relates generally to ultrasound imaging devices and methods and, more specifically to ultrasound imaging devices and methods for imaging a patient's body outside of a traditional medical facility environment.

BACKGROUND

A major challenge for triage of casualties under tactical field care is the absence of lightweight, accurate, intuitive body imaging techniques for trauma patients. Casualty presentation and evaluation on the battlefield or to natural disasters can be complex. This complexity may be further enhanced by the austere diagnostic environments common to theaters of battle. Under these conditions, spinal fractures can be difficult to identify, and pneumothorax issues may be routinely difficult or impossible to accurately diagnose via breath sounds and percussion. Bleeding in the peritoneal, pleural, or pericardial spaces may also occur without obvious clinical warning signs. Distracting obvious open bone injuries and acute altered mental status or unconsciousness can further conceal critical injuries. Accurate triage is essential to allow a medic to stabilize the casualty for transport or to call in a forward surgical team.

Current medical imaging techniques are expensive, often expose patients to potentially harmful radiation, and are mostly non-portable. X-Rays require bulky installation and heavy lead shielding, which as a practical matter is normally only accessible within a clinic or hospital. For example, to fly a portable x-ray or fluoroscopy machine to a remote military base would require one-third the cargo capacity of a Chinook helicopter. Three dimensional ("3-D") imaging from x-rays remains undeployed and requires task-specific a-priori data. Mobile Computed tomography ("mCT") offers high resolution imaging, eliminating shielding needs and is smaller than standard CT imaging systems while still providing 3-D imaging capability. CT is especially helpful in acute head trauma situations for identifying fresh intracranial or subdural bleeding. However, the smaller mobile gantries cannot image the entire body—only the head and neck—and still involve exposing the patient to radiation. Also, because of its large size, mCT is only suitable for intra-hospital use with stable, sedated patients in neurosurgery and intensive care wards. Additionally, contrast agents may be necessary for proper diagnosis. Magnetic Resonance Imaging ("MRI") does not use ionizing radiation, but the large magnet installation largely relegates MRI systems to hospital-based diagnosis methods. The use of MRI is also undesirable in cases involving hemodynamic compromise, making it unfit for many casualty presentations. Furthermore, the time require for using these modalities is substantial, which renders each unsuitable for a quick field assessment or triage.

Ultrasound is a promising option for mobile trauma diagnostics. Ultrasound is widely accepted as a means to visualize internal organ space, and can be used concurrently with other treatments and diagnostics. Ultrasound is a cheaper modality than x-ray, mCT, or MRI, and is portable enough to be packed in a small bag. However, ultrasound is limited to two-dimensional ("2-D") images that require significant expertise to interpret. Focused Assessment with Sonography in Trauma ("FAST") is routinely used for quick assessment of blunt and penetrating chest and abdominal trauma, and is specifically indicated for identifying potential pericardial effusion, intraperitoneal bleeding, or bleeding in the pleural space (hemothorax). Assessment of pneumothorax is available in an extended-FAST ("E-FAST") protocol.

In civilian settings, FAST has been used to decrease CT and diagnostic peritoneal lavage without risk to the patient. In a military setting, ultrasound has been proven useful in single-surgeon hospital-based trauma studies. Recently, ultrasound has been deployed in the theater experimentally in certain battalions with great success in 2-D soft tissue imaging. This deployment of ultrasound has benefited the local civilian war wounded as well. However, ultrasound has been relegated to non-emergent diagnostics such as shrapnel identification in wounds or late identification of closed limb fractures at the bedside. It has recently been suggested that ultrasound could be used to address bone fracture identification in the field, but this would require that the user have extensive specialized training and expertise.

Accurate diagnoses are difficult and yet most essential with a complicated initial presentation in the field or in a hospital emergency department. However, to date no available modality has proven able to reliably detect bone skeletal trauma—which is often undetectable by a physical examination—along with other potential life-threatening internal visceral injuries that produce air and blood collections in the patient.

SUMMARY

In an embodiment of the invention, an ultrasound cover is provided for use with an ultrasound imaging system. The ultrasound cover includes a central layer configured to conform to a shape of a patient's body and a plurality of ultrasound sensors positioned within the central layer.

In another embodiment of the invention, a method of examining a patient using ultrasound is provided. The method includes positioning an ultrasound cover on the patient. The ultrasound cover includes a central layer configured to conform to a shape of a patient's body and a plurality of ultrasound sensors positioned within the central layer. The method further includes acquiring raw RF ultrasound signals from at least one of the plurality of ultrasound signals, extracting at least one echo from the raw RF ultrasound signals, and creating a 3-D model of a portion of the anatomy of the patient from the raw RF ultrasound signals.

In yet another embodiment of the invention, an ultrasound diagnostic system is presented. The ultrasound diagnostic system includes an ultrasound cover that has a central layer configured to conform to a shape of a patient's body and a plurality of ultrasound sensors that are positioned within the central layer. The ultrasound diagnostic system further includes a computer having access to an orthopedic-specific dataset. The data set includes data relating to a plurality of patient bones that statistically models the morphology of a bone. The computer is configured to acquire and search ultrasound data to locate bony boundaries by detecting specific echo patents and comparing the ultrasound data to the orthopedic-specific dataset.

DETAILED DESCRIPTION

Figure 1:
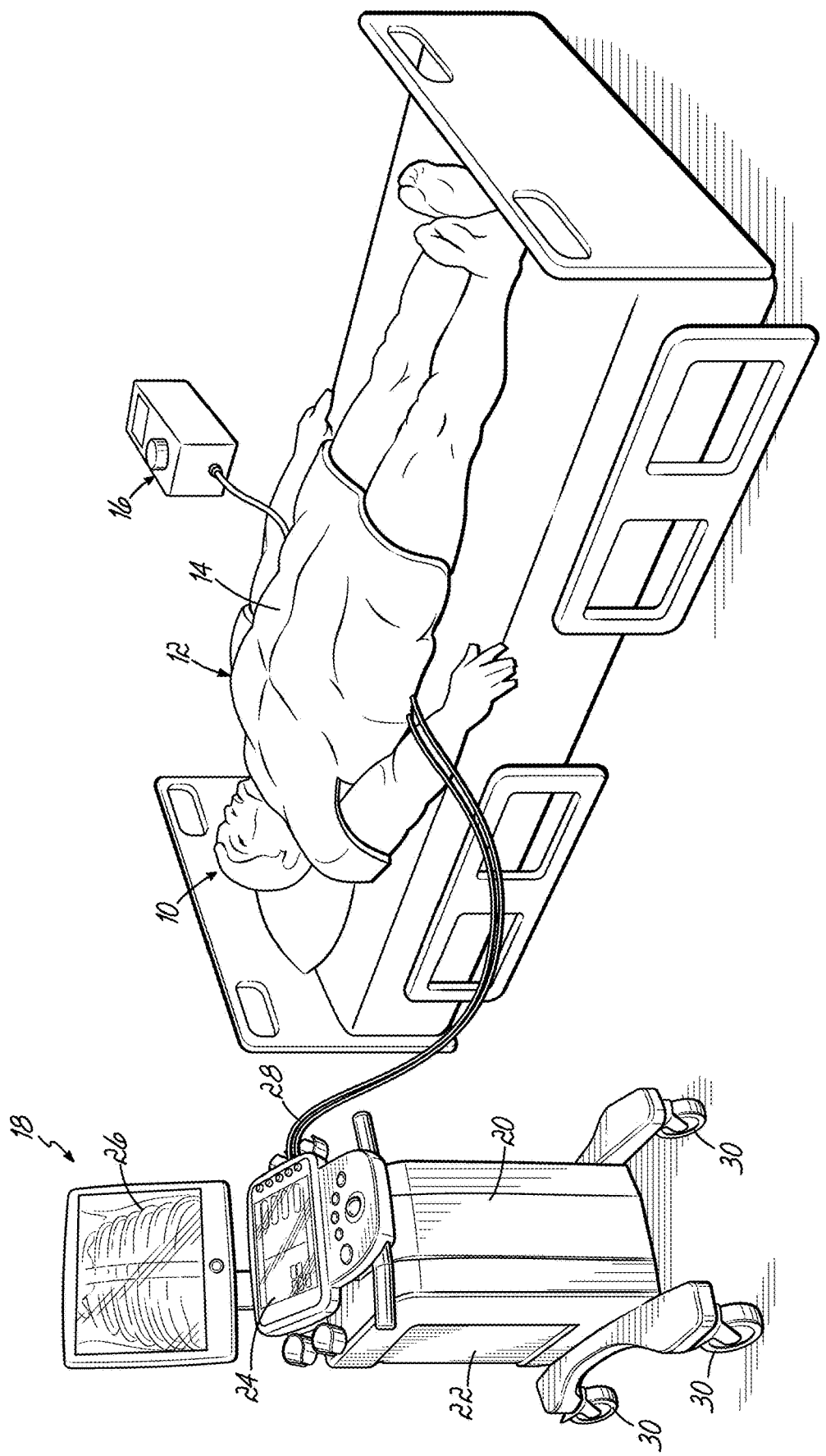
FIG. 1 is a perspective view of a patient with an ultrasound imaging system in accordance with an embodiment of the invention.

Referring now to FIG. 1, a patient 10 is shown covered by an ultrasound imaging device including an ultrasound cover 12 with a top layer 14 in accordance with one embodiment of the invention. Also shown are a vacuum system 16 and an ultrasound imaging system 18 for coupling to the ultrasound cover 12. The ultrasound imaging system 18 should be configurable such that the user may access acquired RF ultrasound data. One suitable instrument may, for example, include the diagnostic ultrasound model SonixRP by Ultrasonix Inc. (Richmond, British Columbia, Canada). The ultrasound imaging system 18 includes a housing 20 containing a controller, (for example, a computer 22), an energy or power source (not shown), a user input device 24, an output device (for example, a monitor 26), and one or more ultrasound connector cables 28 for coupling to the cover 12. The coupling connection between the computer and cover 12 might also be wireless and handled by a suitable wireless connection. The housing 20 may include caster wheels 30 to facilitate transporting the ultrasound imaging system 18.

The patient 10 is shown in an unclothed and supine state to facilitate examination of the body in situations involving trauma. The patient might also be in the prone state to evaluate the spine or to address how the patient might be positioned in an actual trauma scenario. Internal injuries may be difficult to detect unless there is significant swelling in the injured body part or region. To provide improved diagnostic capabilities, an ultrasound cover 12 in accordance with an embodiment of the invention may be operable in at least one of three modes: (1) a bone trauma mode, such as for detection of bone fractures, e.g., cervical spine or rib fractures; (2) a pneumothorax mode, e.g., for detecting air pockets in the chest and abdominal regions; and (3) an intra-peritoneal bleeding or hemothorax mode. Typically, all three modes would be used for diagnosing the patient 10, but it is also possible for single modes to be used selectively in accordance with other aspects of embodiments of invention.

Figure 2:
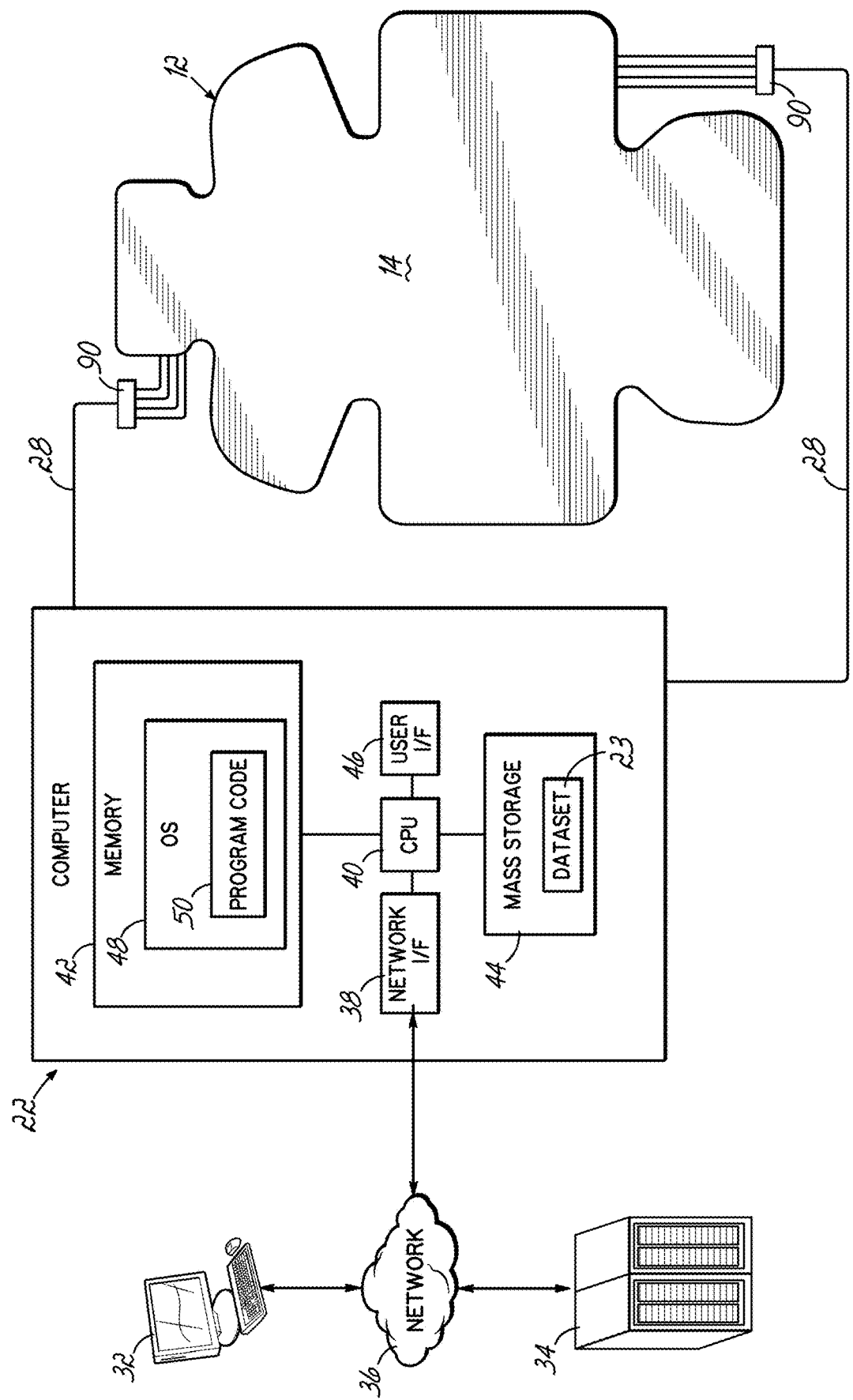
FIG. 2 is a diagrammatic view of a computer system suitable for use with the ultrasound system and ultrasound cover in accordance with an embodiment of the invention.

Referring now to FIG. 2, the computer 22 of the ultrasound imaging system 18 is shown coupled to an ultrasound cover 12 in the form of a vest. The computer 22 may be considered to represent any type of computer, computer system, computing system, server, disk array, or programmable device such as multi-user computers, single-user computers, handheld devices, networked devices, or embedded devices, etc. The computer 22 may be implemented with one or more networked computers 32 or networked storage devices 34 using one or more networks 36, e.g., in a cluster or other distributed computing system through a network interface 38 (illustrated as "NETWORK I/F"). For brevity's sake, the computer 22 will be referred to simply as "computer," although it should be appreciated that the term "computing system" may also include other suitable programmable electronic devices consistent with embodiments of the present invention.

The computer 22 typically includes at least one processing unit 40 (illustrated as "CPU") coupled to a memory 42 along with several different types of peripheral devices, e.g., a mass storage device 44, a user interface 46 (illustrated as "User I/F"), which may include the input device 24 and the monitor 26, and the Network I/F 38. The memory 42 may include dynamic random access memory ("DRAM"), static random access memory ("SRAM"), non-volatile random access memory ("NVRAM"), persistent memory, flash memory, at least one hard disk drive, and/or another digital storage medium. The mass storage device 44 is typically includes at least one hard disk drive and may be located externally to the computer 22, such as in a separate enclosure, in one or more of the networked computers 32, or one or more of the networked storage devices 34 (for example, in a database server).

The CPU 40 may be, in various embodiments, a single-thread, multi-threaded, multi-core, and/or multi-element processing unit as is well known in the art. In alternative embodiments, the computer 22 may include a plurality of processing units that may include single-thread processing units, multi-threaded processing units, multi-core processing units, multi-element processing units, and/or combinations thereof as is well known in the art. Similarly, the memory 42 may include one or more levels of data, instruction, and/or combination caches, with caches serving the individual processing unit or multiple processing units as is well known in the art.

The memory 42 of the computer 22 may include an operating system 48 (illustrated as "OS") to control the primary operation of the computer 22 in a manner that is well known in the art. The memory 42 may also include at least one application, component, algorithm, program, object, module, or sequence of instructions referred to herein as program code 50. Program code 50 typically comprises one or more instructions that are resident at various times in the memory 42 and/or the mass storage device 44 of the computer 22, and that, when read and executed by the CPU 40, causes the computer 22 to perform the steps necessary to execute steps or elements embodying the various aspects of the present invention.

Those skilled in the art will recognize that the environment illustrated in FIG. 2 is not intended to limit the present invention. Indeed, those skilled in the art will recognize that other alternative hardware and/or software environments may be used without departing from the scope of the present invention.

Figure 3:
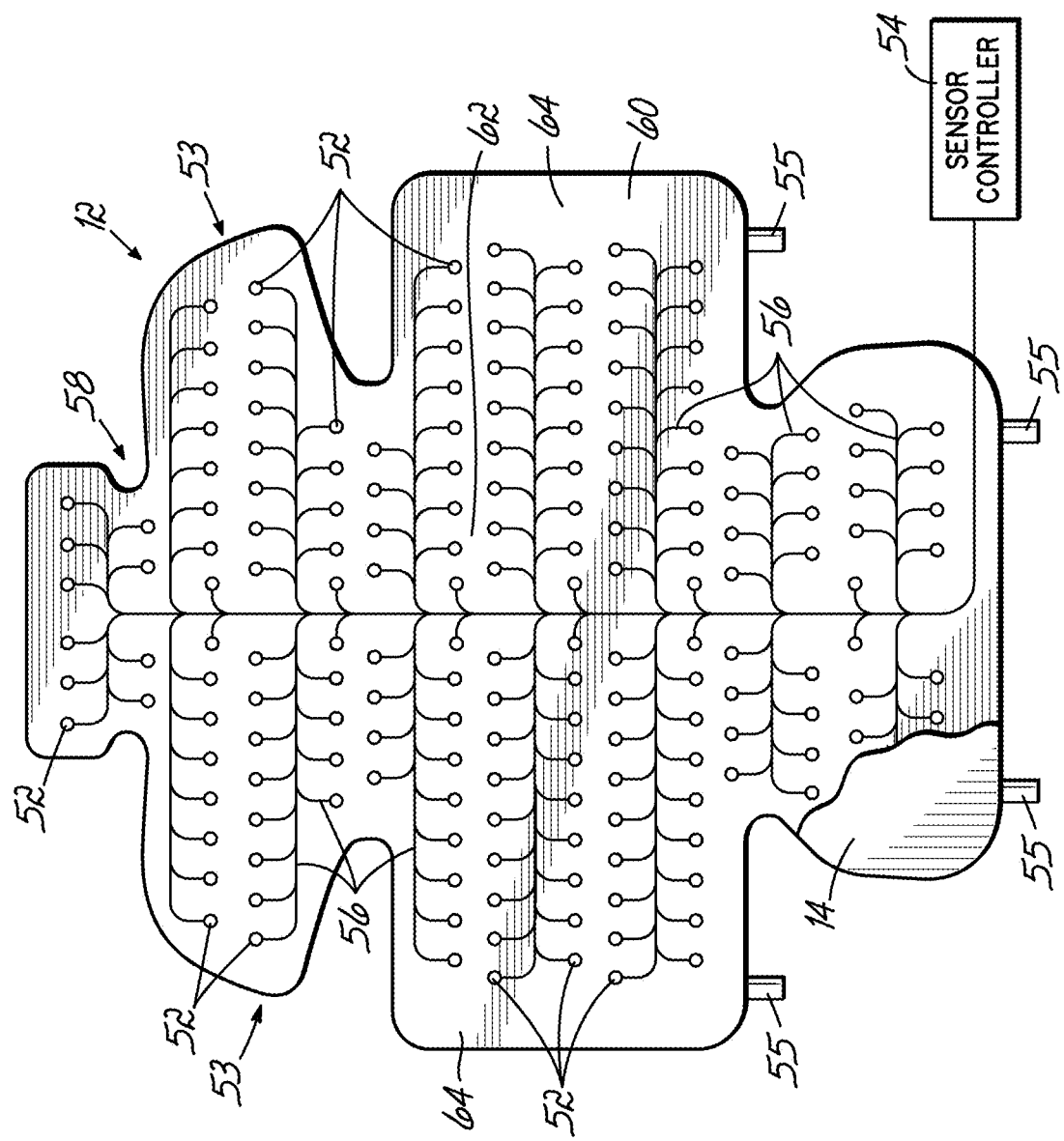
FIG. 3 is a top view of the ultrasound cover of FIG. 1.
Figure 4:
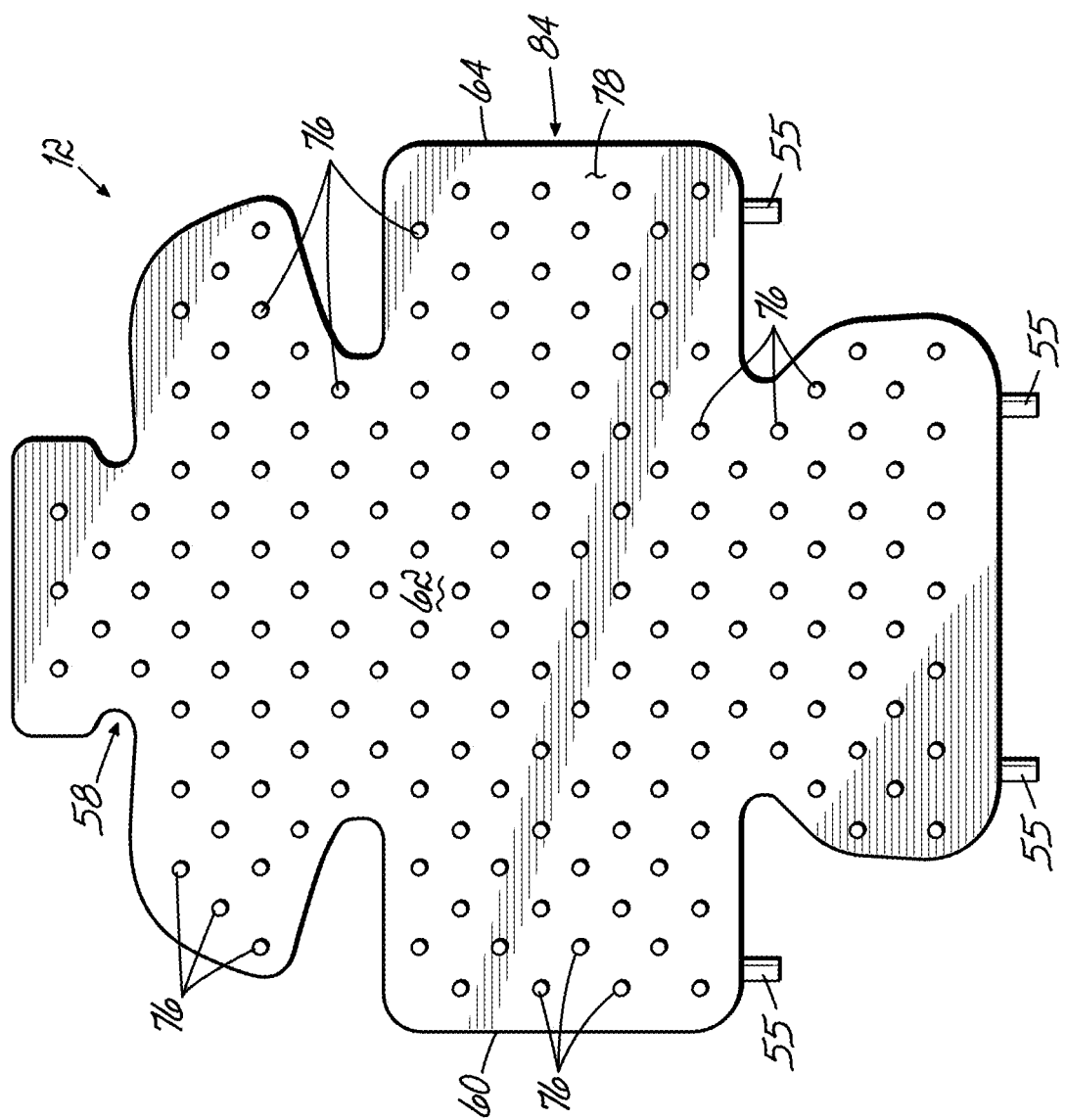
FIG. 4 is a bottom view of the ultrasound cover of FIG. 1.

An embodiment of the ultrasound cover 12 suitable for rapid triage imaging is shown in more detail in FIG. 3. Although the ultrasound cover 12 is specifically illustrated in this embodiment as a vest configuration, the cover 12 may alternatively be a jacket, a blanket, or other configuration or device that is in a form that covers at least a portion of the body. The cover 12 includes a plurality of ultrasound transducers or sensors 52 positioned on at least a portion of the cover 12. As described in greater detail below, the exemplary cover 12 is operable to non-invasively and quickly image the thoraco-abdominal and pelvic areas of a patient 10 for identification of internal injuries. Because the cover 12 is lightweight and portable, the cover 12 may be placed against the body of the patient 10, and is easily switchable between multiple modes of operation. One or more of the plurality of sensors 52 may be coupled to a sensor controller 54 by wires 56. The cover 12 may also include one or more vacuum ports 55 for coupling the cover 12 to the vacuum system 16. As shown in FIGS. 3 and 4, the cover 12 may be shaped to conform to a particular portion of the patient's body, such as the neck and thorax, abdomen and pelvis, for example. To this end, the ultrasound cover 12 may include a neck region 58, wings 53, a mid-section 62, and abdominal flaps 64 for imaging the neck, thorax, abdomen, kidneys and liver and spleen of the patient 10.

Figure 5:
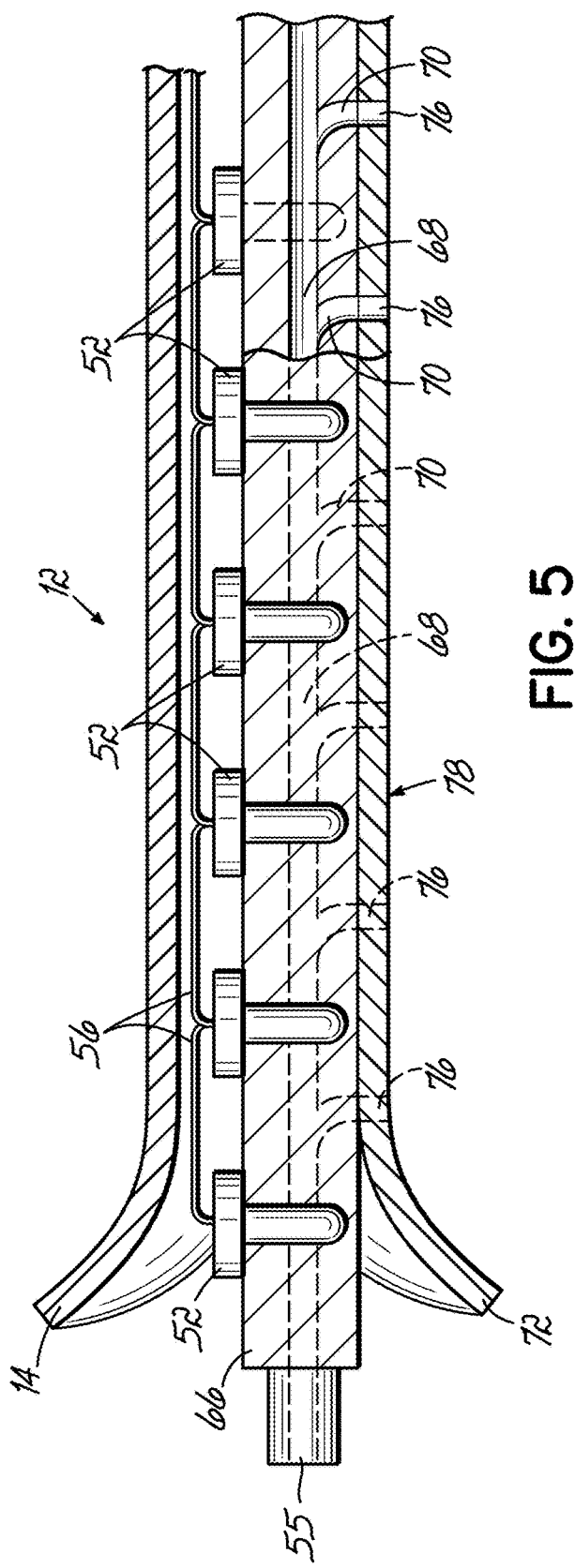
FIG. 5 is a cross-sectional view of a portion of the ultrasound cover of FIG. 1.

Referring now to FIGS. 4 and 5, a bottom view of the cover 12 is presented in FIG. 4, and a cross-sectional view of the cover 12 is presented in FIG. 5. The sensors 52 may be arranged and positioned within a central layer 66 of the cover 12 that includes a plurality of vacuum passages 68 therein. In accordance with one aspect of the invention, the central layer 66 may be comprised of a material that can be contoured to the injured patient's body while retaining sufficient rigidity to structurally support the sensors 52. The vacuum passages 68 may terminate in a plurality of apertures 70 along a bottom surface of the central layer 66 to allow the cover 12 to be conformed to the patient's shape by drawing air through the vacuum passages 68.

A disposable vacuum membrane 72 may be removably coupled to the bottom of the central layer 66 and positioned for contacting the patient 10. The disposable membrane 72 provides for sanitary use of the cover 12, and may include a silicone filling or layer without perforations, a silicone layer with perforations 76, or a flexible polymeric sheet comprised of, for example, polyurethane. For embodiments in which the membrane includes perforations 76, the perforations 76 may be configured to couple the vacuum passages 68 to a bottom surface 78 of the membrane 72 so that the ultrasound cover 12 can be held in place by drawing air through the vacuum passages 68. To this end, the perforations may be aligned with the plurality of apertures 70. In any case, the vacuum membrane 72 is configured to provide a good acoustic matching impedance to facilitate ultrasound pulse penetration into the patient 10. The matching impedance provided by the membrane 72 may also improve ultrasound echo transmission and reception. The use of ultrasound gel may therefore not be necessary with the vacuum membrane 72; however, ultrasound gel may be used with the membrane 72 if desired.

The vacuum ports 55 may extend externally from the central layer 66, and are configured to be coupled to the vacuum system 16 so that the vacuum system 16 can draw air though the vacuum passages 68. One suitable vacuum system 16 for use in embodiments of the invention may be, for example, the LIMBLOGIC VSI by The Ohio Willow Wood Co. (Mt. Sterling, Ohio). Accordingly, the central layer 66 may, while under vacuum, conform to the shape of the patient's body for improving sensor contact with the patient 10 and improving signal-to-noise ratios.

In an alternative embodiment, the disposable membrane 72 may be an adhesive layer that, much like a disposable bandage, temporarily adheres to the patient's skin during imaging. Still other embodiments may include a weighted substrate, such as a lead x-ray apron, that is positioned above the ultrasound cover 12 so as to apply a force that conforms the cover 12 to the shape of the patient's body. For example, top layer 14 might incorporate a weighted layer or substrate to conform the cover 12 to a patient 10. Still other embodiments may include adhesive strips (not shown, but, for example, VELCRO) that are used to secure the ultrasound cover 12 around at least a portion of the patient's body.

The top layer 14 of the ultrasound cover 12 may be coupled to the central layer 66 to provide protection to various electrical components associated with the sensors 52, such as the connecting wires 56. The top layer 14 may also be at least partially removable to facilitate sensor replacement or adjustment, or otherwise allow access to the sensors.

Figure 6C:
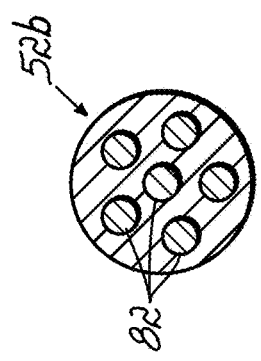
FIGS. 6A-6C illustrate two embodiments of an ultrasound sensor for use with the ultrasound cover of FIG. 1.
Figure 6B:
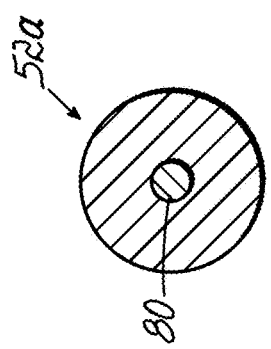
Figure 6A:
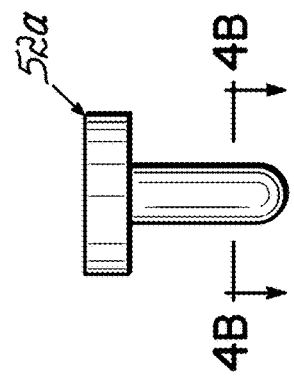

The sensors 52 may be either static or dynamic. That is, the sensors 52 may be fixed or may be moveable with respect to the ultrasound cover 12. One embodiment may include round sensors 52 having a single element 80 as shown in FIGS. 6A and 6B. Another embodiment may have sensors 52 that include multiple elements 82 as shown in FIGS. 6A and 6C. Although six elements are shown in FIG. 6C, persons having ordinary skill in the art will understand that any number of elements may be used, and that these elements may be arranged in any suitable design or pattern. Embodiments of the invention are therefore not limited to a specific number or configuration of sensor elements. The sensors 52 may be high or low frequency sensors. For example the sensors may include low frequency sensor transducers (e.g., a sensor having 64 elements) for deeper Near Field Depth ("NFD") detection of air and blood. In an alternative embodiment, the sensor 52 may include high frequency sensor transducers for shallower but higher resolution imaging that provide a shallower NFD. High and low frequency sensors may be located together for identifying different injuries.

Figure 7:
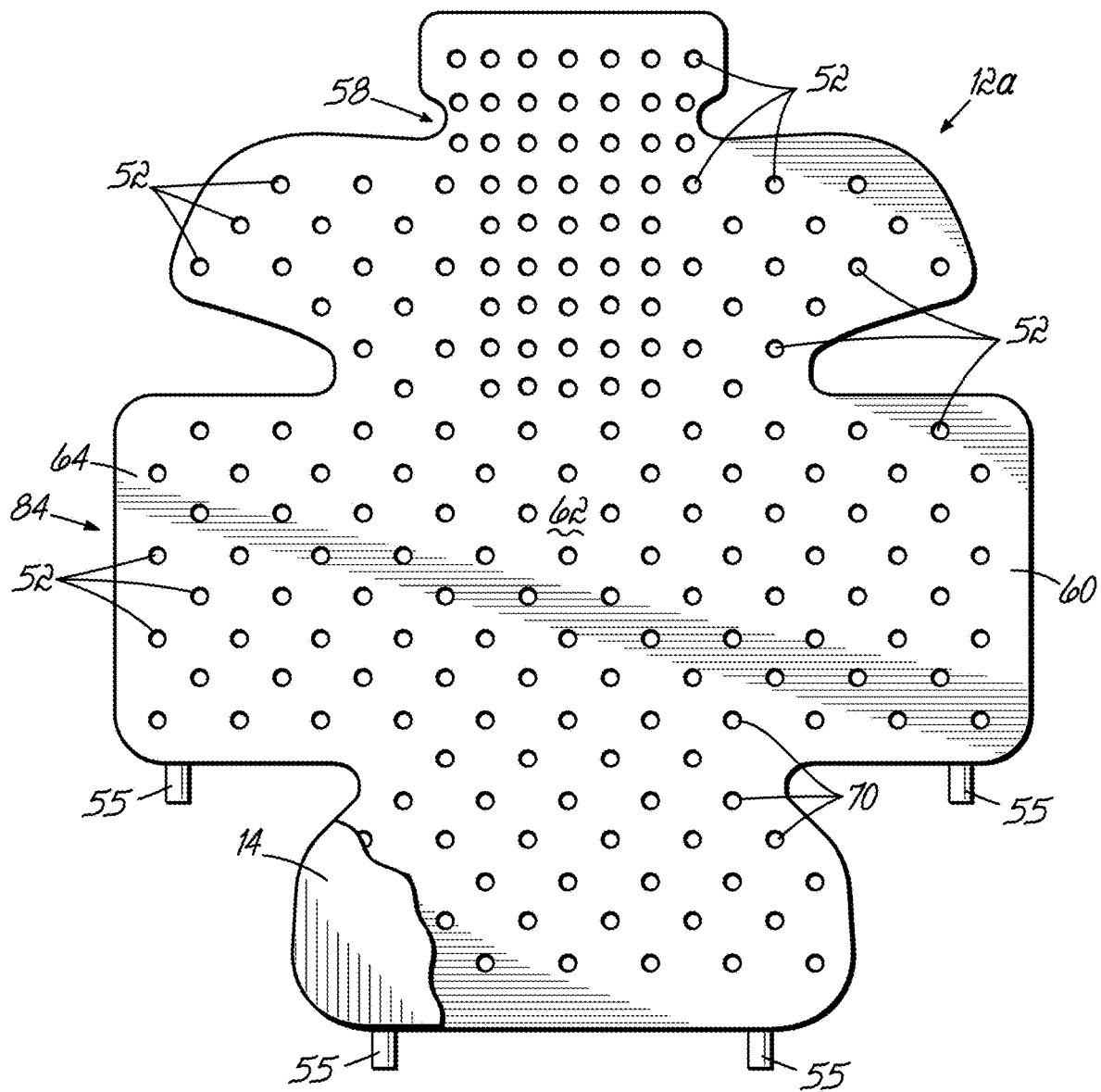
FIGS. 7-9 are top views of ultrasound covers in accordance with embodiments of the invention.
Figure 8:
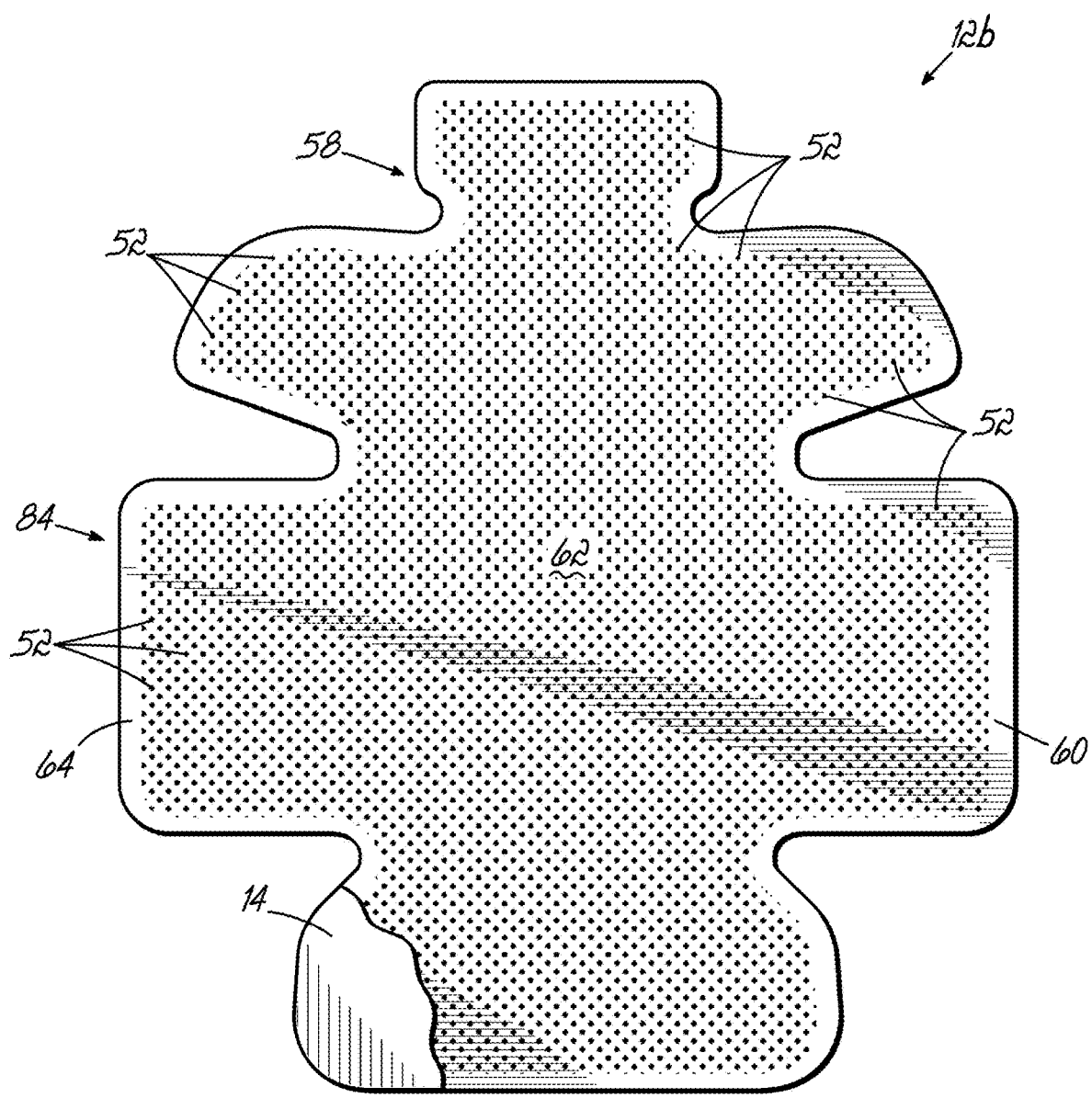
Figure 9:
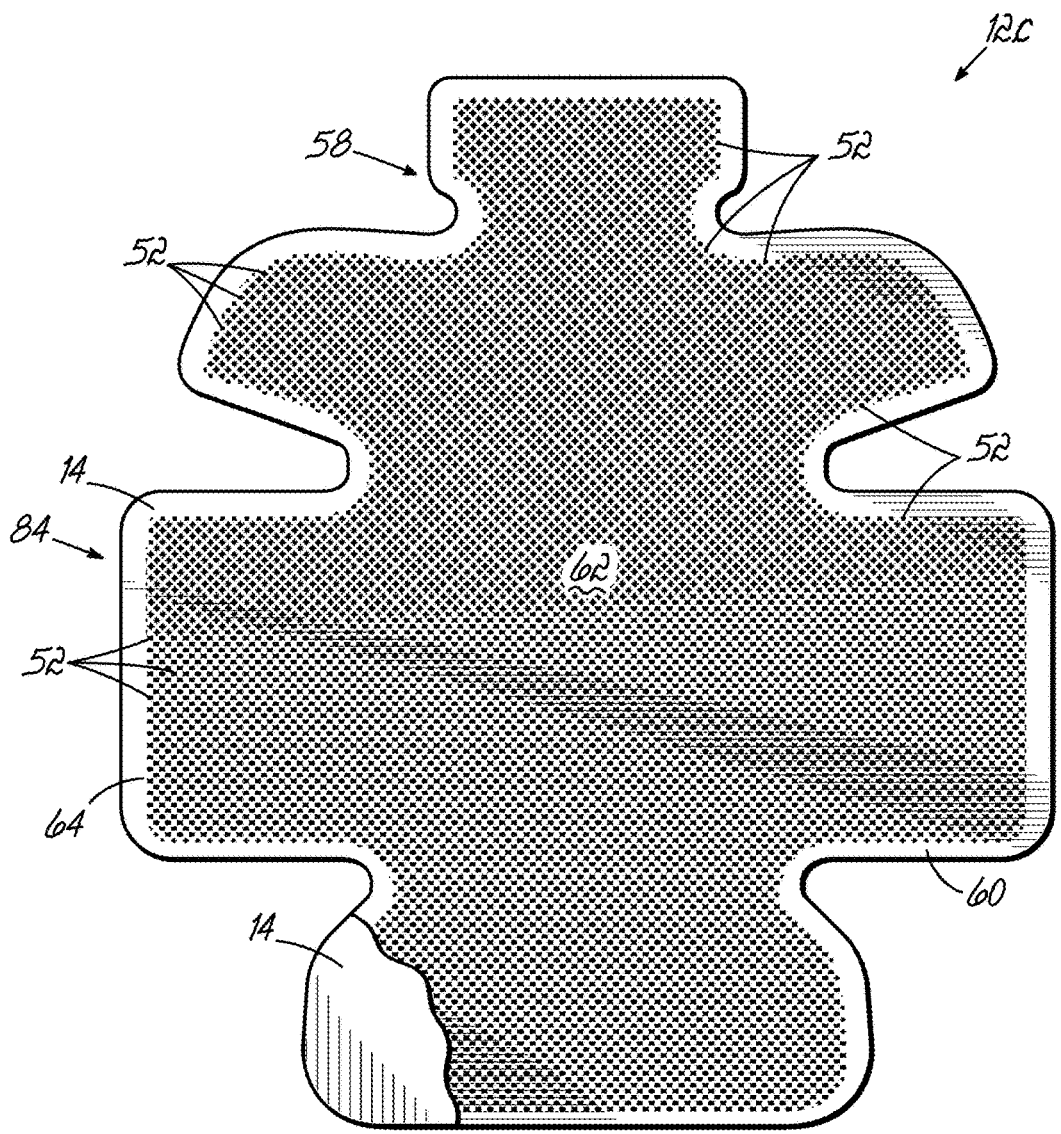

One or more of the round sensors 52 may be positioned along the ultrasound cover 12 in a pattern having a generally uniform density, as shown in FIG. 3. In an alternative embodiment, the density of the sensors 52 may vary within one or more areas or portions of the ultrasound cover 12. For example, as shown in FIG. 7, a first portion of the ultrasound cover 12a, illustrated here as the neck region 58, has a higher density of sensors 52 than a second or a remaining portion 84 of the cover 12a. This higher sensor density may provide higher resolution imaging of the neck and upper cervical spine of the patient 10. Because the areas of the ultrasound cover 12a having higher sensor densities may have less space to accommodate the vacuum passages 68, these high sensor density areas may include fewer or no vacuum passages 68 as compared to other regions of the ultrasound cover 12a. In still other embodiments, such as illustrated in FIGS. 8 and 9, vests 12b, 12c may include higher sensor densities that generally cover the entire active area of ultrasound cover 12b, 12c. However, in alternative embodiments, these higher sensor densities may be localized to specific body areas of the ultrasound cover 12 similarly as shown in FIG. 7. Covers with higher densities of sensors in the thoracic region may be chosen for patients suspected of injury to a specific body region.

Figure 10:
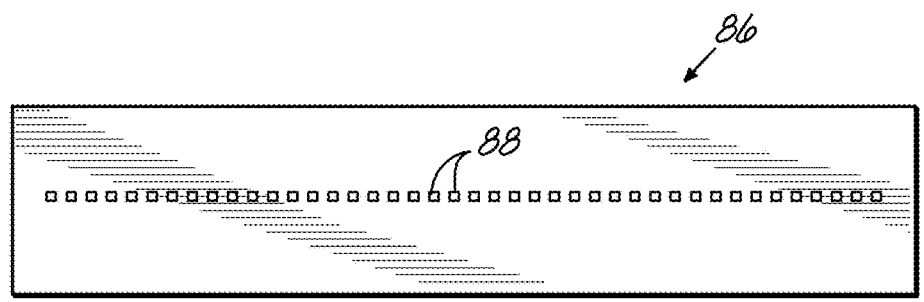
FIG. 10 illustrates an embodiment of a sensor as a linear multi-element ultrasound sensor in accordance with an embodiment of the invention.
Figure 11:
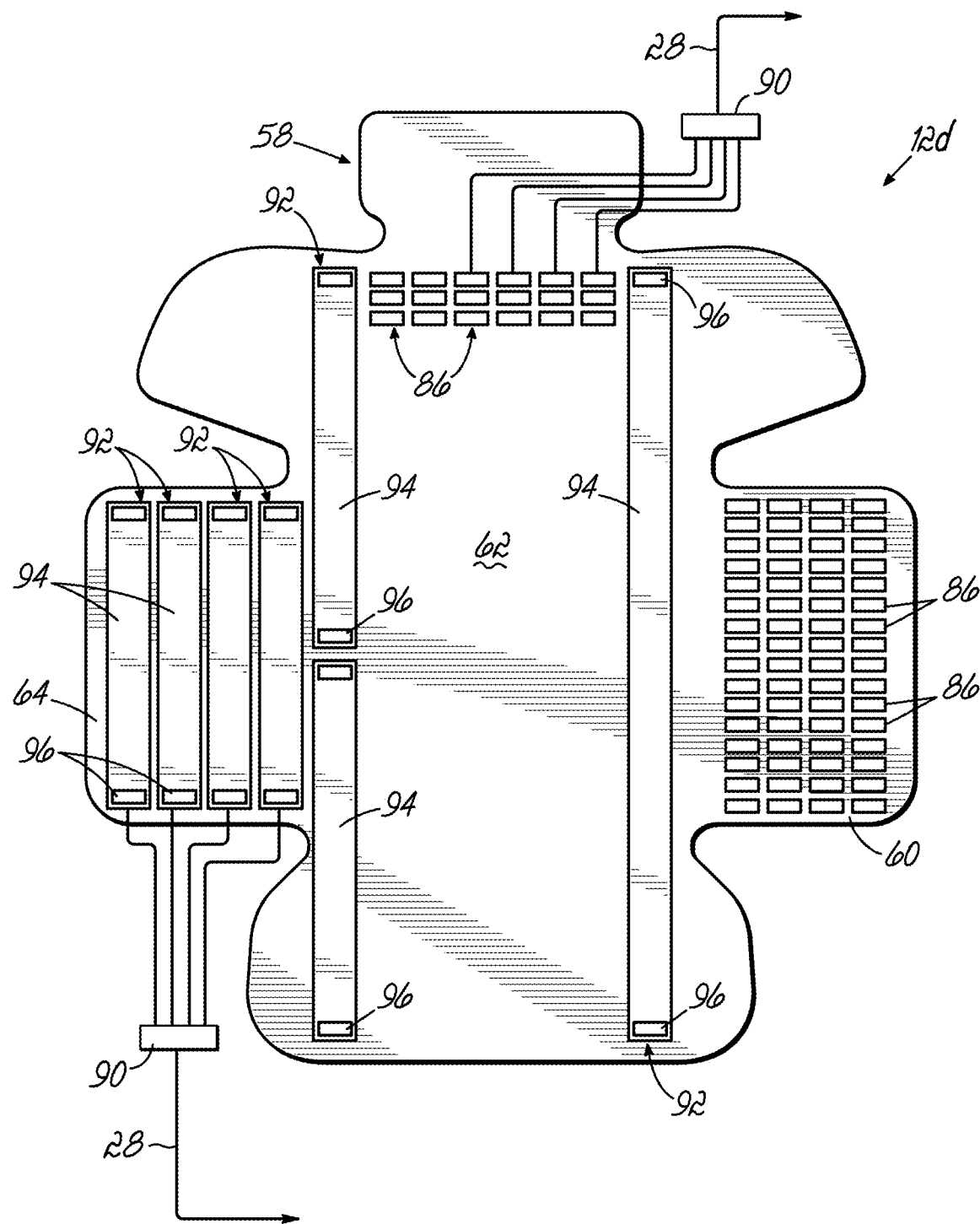
FIGS. 11-13 are top views of ultrasound covers including dynamic sensors in accordance with alternative embodiments of the invention.
Figure 12:
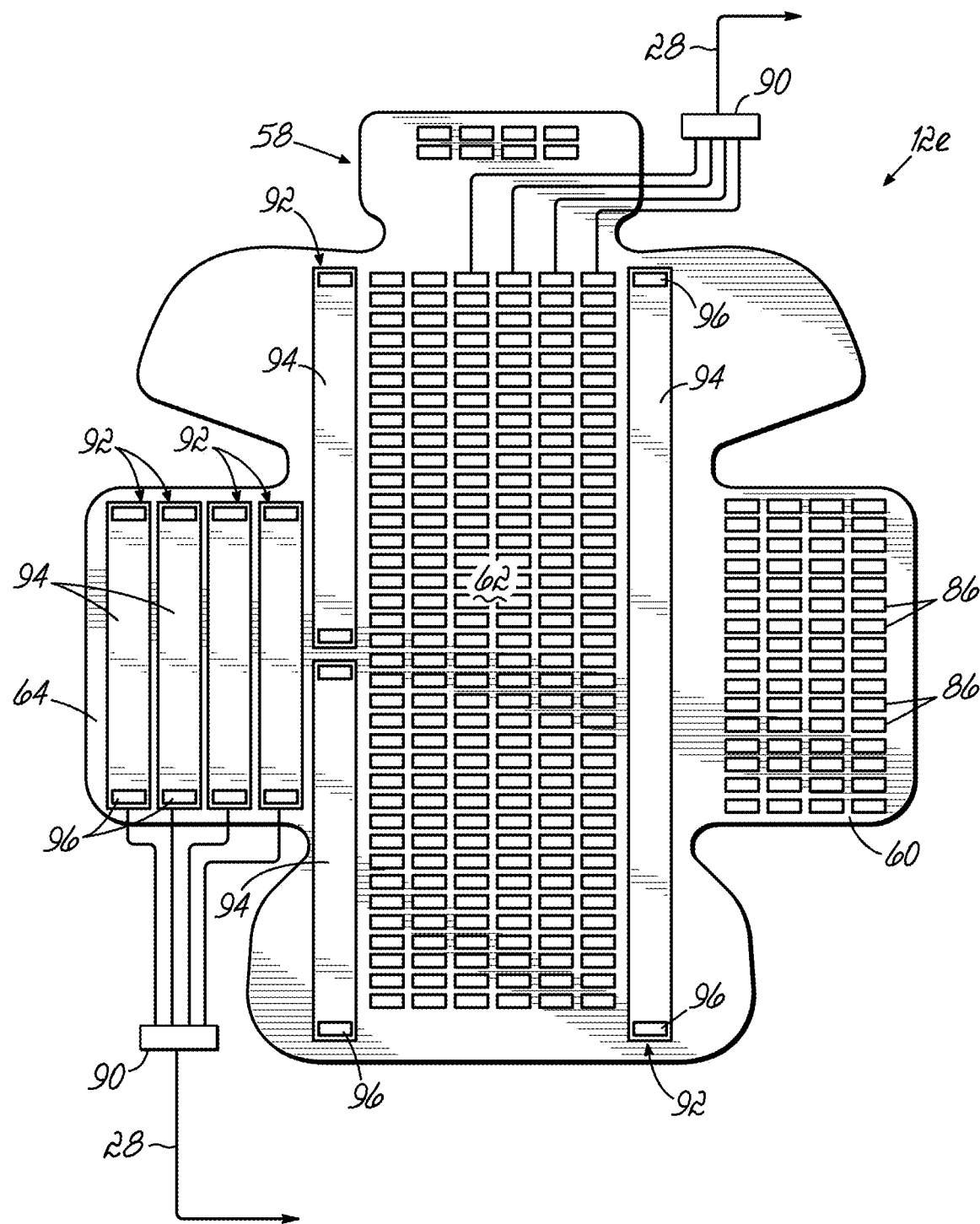
Figure 13:
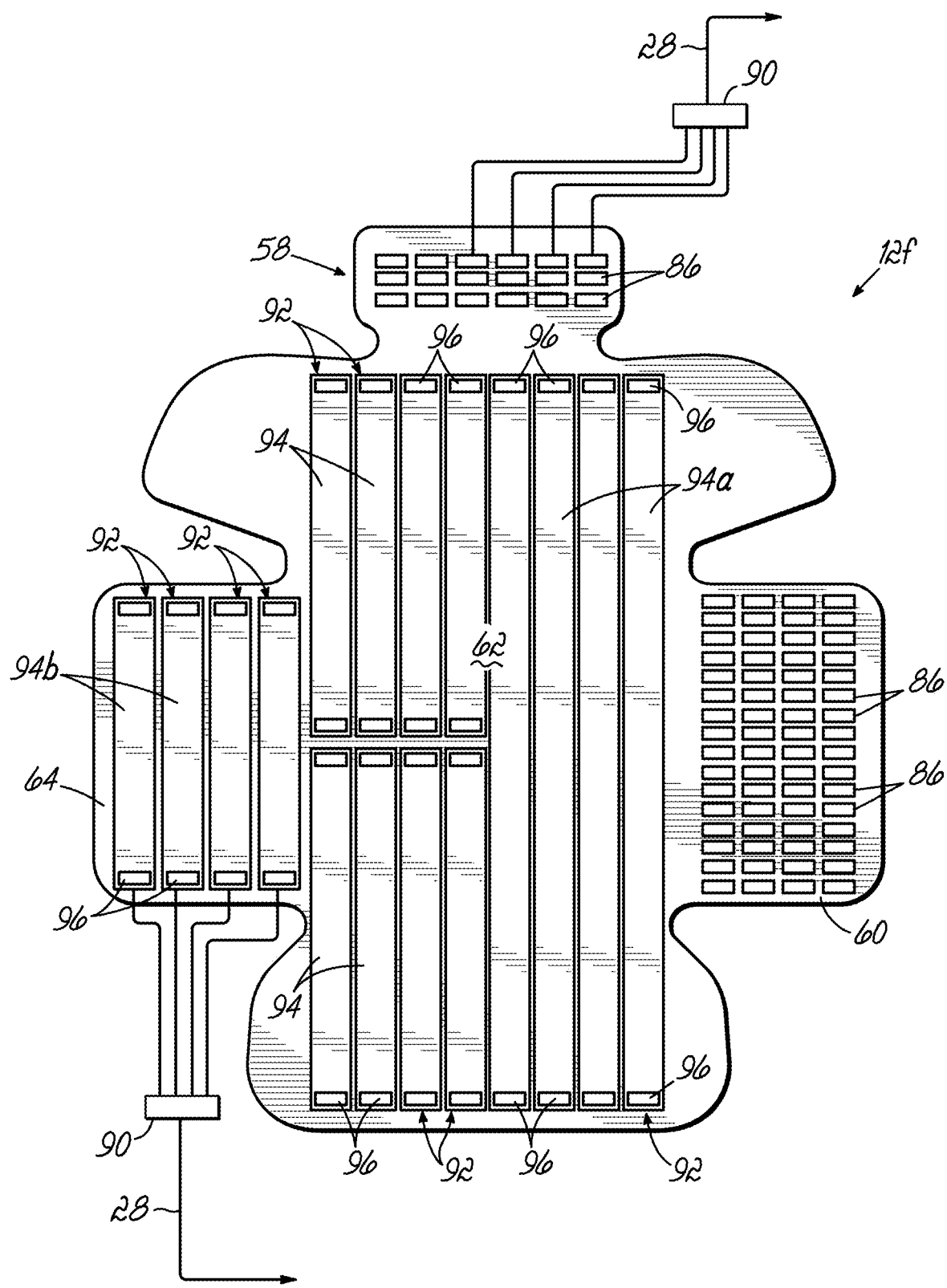

Another embodiment of an ultrasound transducer or sensor 52 is illustrated in FIG. 10 as a linear element sensor 86 having a plurality of elements 88 in a generally linear configuration. Referring now to FIGS. 11-13, which show top views of covers 12d-12f, and FIG. 14, which shows a representational cross-sectional view of the covers 12d-12f, one or more of these linear element sensors 86 may be positioned on at least a portion of an ultrasound cover 12d, 12e, 12f for higher resolution imaging. Persons having ordinary skill in the art will understand that such an embodiment may include complex electronics and may require multiple ultrasound connectors 90 to facilitate coupling the sensors 52, 86 to the ultrasound imaging system 18 via one or more ultrasound connector cables 28. Linear element sensors 86 may be positioned throughout the ultrasound cover 12d, or may be localized for high resolution imaging of specific regions of the patient 10. For example, a plurality of the sensors 86 may be positioned on the left wing 60 of the ultrasound cover 12d to acquire high resolution ultrasound signals from an area proximate to the patient's left kidney or spleen. As shown in FIG. 11, an embodiment of an ultrasound cover 12e may include multiple pluralities of linear element sensors 86 grouped in areas along the neck region 58, the mid-section 62, and the left wing 60, for imaging the neck, thorax, and the left kidney or spleen portion, respectively.

In alternative embodiments of the invention, dynamic sensors may be implemented. The covers 12d-12f each includes one or more dynamic sensors 92 in accordance with an embodiment of the invention. The dynamic sensors 92 may include a track 94 and one or more mobile sensors 96 that are configured to scan the whole body (DYNamicFull or "DYNF"), such as sensors with tracks 94a, or only partial body segments (DYNamicPartial, "DYNP"), such as sensors with tracks 94b. Accordingly, the ultrasound covers 12d-12f may be comprised entirely of DYNF sensors, entirely DYNP sensors, or may have at least one portion having DYNF dynamic sensors and at least one portion having DYNP sensors.

Figure 14:
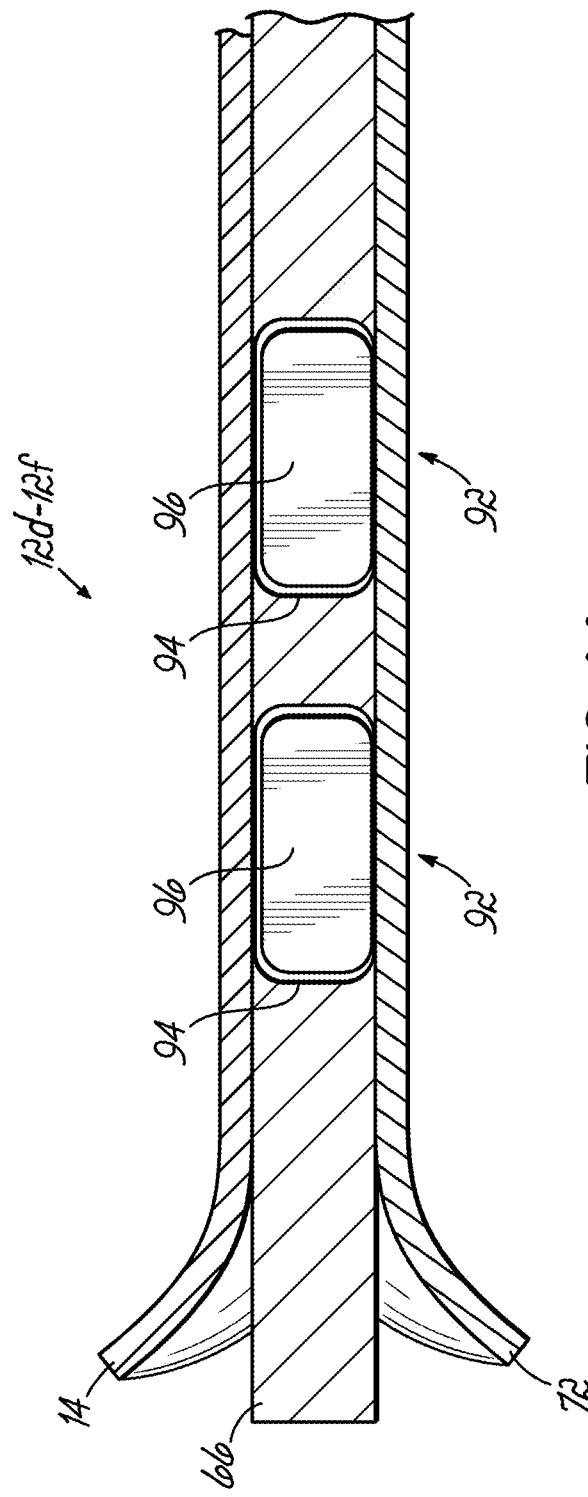
FIG. 14 is a cross-sectional view of a portion of an ultrasound cover of FIGS. 11-13.

As best shown in FIG. 14, the track 94 is typically located in the central layer 66. The at least one mobile sensor 96 may be any suitable ultrasound sensor, such as a multi crystal linear element similar to the linear element sensor 86 illustrated in FIG. 10. The one or more mobile sensors 96 may be configured to move along the track 94. The track length may be configured as desired, with a longer track 94a being used for imaging the whole length of the body, and a shorter track 94b being used to image a smaller portion of the body or body segment. The mobile sensor 96 may be a low frequency sensor transducer (e.g., a sensor having 64 elements) for deeper Near Field Depth ("NFD") detection of air and blood. In an alternative embodiment, the mobile sensor 96 may be a high frequency sensor transducer for shallower but higher resolution imaging that provides a shallower NFD. High and low frequency sensors may be located at opposing ends of a single track 94 for sequential imaging and for identifying different injuries.

Various embodiments of ultrasound covers 12d-12f having one or more dynamic sensors 92 may also include static linear sensors 86, as shown in FIGS. 11-13. More particularly, in FIG. 13, a first plurality of static sensors 86 is positioned in the neck region 58, a plurality of DYNF sensors 92 are positioned along the left half of the mid-section 62, a first plurality of DYNP sensors 92 are positioned along the right half of the mid-section 62, a second plurality of DYNP sensors 92 are positioned on a right abdominal flap 64, such as for visualizing the liver, and a second plurality of static sensors 86 are positioned on the left abdominal flap, such as for visualizing the spleen.

The use of the dynamic sensors 92 may decrease the number and complexity of the sensor electronics as compared to the static sensors 86 described previously. However, use of dynamic sensors 92 may also increase scan times, and may require the addition of actuators (not shown) for moving the mobile sensors 94 in their respective tracks 96.

In operation, the ultrasound cover 12 may be positioned on the patient 10 and connected to the ultrasound imaging system 18 by coupling the ultrasound connectors 90 to the system 18 via connector cables 28. If vacuum assisted attachment of the ultrasound cover 12 to the patient 10 is desired, the vacuum system 16 may be coupled to the one or more vacuum ports 55 and activated. In cases where the vacuum system 16 is coupled to less than all the vacuum ports 55, the unused vacuum ports 55 may be plugged or may include one-way valves that prevent air from entering the unused ports. The ultrasound imaging system 18 should be configurable such that the user may access acquired radiofrequency ("RF") ultrasound data. To obtain ultrasound data from the patient 10, an ultrasound signal is transmitted from the system 18 via the connector cables 28 and connector 90 to one or more sensors 52, 86, 92. The one or more sensors thereby generate an ultrasound signal that is transmitted into the patient 10. A received RF echo may then be transmitted along the cable 28 to the computer 22 of ultrasound imaging system 18 for processing in accordance with an embodiment of the present invention.

To use the highest available contrast and spatial resolution in the data, the computer 22 utilizes the acquired, raw RF signals to automatically extract the bone or other tissue contours from the ultrasound scans rather than relying on conventional 2-D B-mode images. Data processing is performed as scans are received from the transducers with no lag in visualization of the 3-D image.

An orthopedic-specific dataset 23 may be maintained in a database or one or more data structures in the mass storage device 44 of computer 22, or on one or more of the external devices 32, 34. The orthopedic-specific data set 23 may include data relating to a plurality of patient bones (e.g., over one hundred) that statistically models the morphology of each bone. With this a priori information serving as a training set, algorithms search the ultrasound data as the data is acquired to locate bony boundaries. This real-time image analysis enables the display of 3-D bones overlaid with 2-D image slices as a scan is performed, making the imaging intuitive and easy to read. Where field of view of the scan is limited, the bone may still be visualized based on its most likely shape given the available data. Discontinuities can easily be detected, alerting the user to fractures.

Both static and mobile image features may be acquired and displayed for identifying areas with these characteristics within the scan field of view. Especially problematic areas may also be highlighted. Probabilistic signal modeling allows intelligent processing of new data based on a priori anatomic information. A suitable system for use with embodiments of the present invention may include, for example, the system and/or systems PCT Patent Application Ser. No. PCT/US11/46318, entitled METHOD AND APPARATUS FOR THREE DIMENSIONAL RECONSTRUCTION OF JOINT USING ULTRASOUND, filed on Aug. 2, 2011; U.S. patent application Ser. No. 12/364,267, entitled NONVINVASIVE DIAGNOSTIC SYSTEM, filed on Feb. 2, 2009; and U.S. patent application Ser. No. 13/196,701, entitled NONINVASIVE DIAGNOSTIC SYSTEM, filed on Aug. 11, 2011; all such applications are incorporated herein by reference in their entireties.

Figure 15:
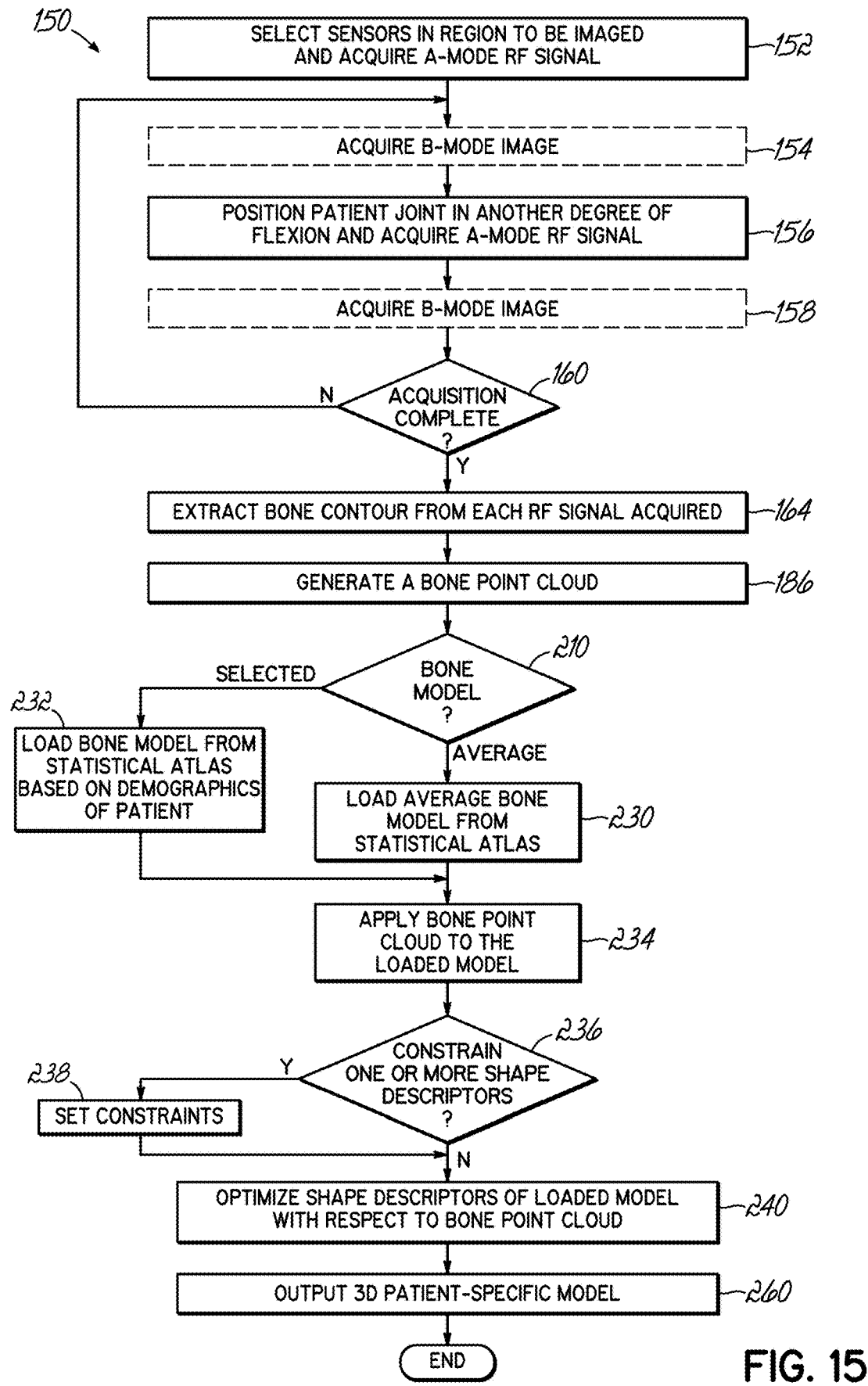
FIG. 15 is a flow chart illustrating an exemplary method of acquiring an A-mode ultrasound RF signal and generating a 3-D patient-specific anatomical model.

Turning now to FIG. 15, one possible embodiment of the invention may utilize a method 150 of acquiring ultrasound data for construction of a 3-D patient-specific anatomical model. The method begins with acquiring a plurality of RF signals 142 (FIG. 17A) from an A-mode ultrasound beam scan of a region of the patient 10. In block 152, one or more sensors 52, 92 in the area to be imaged is selected to acquire the RF signals for creating the 3-D patient-specific model of that region of the patient. The sensors 52, 92 may be selected based on their position at two or more locations in proximity to the selected region of the patient 10. These sensors may be located on the patient's epidermis adjacent to the region to be imaged for acquisition of an A-mode RF signal. Although the acquired signal includes a plurality of RF signals 142, for convenience, the RF signals 142 are sometimes referred to herein in singular form.

The position of the patient 10 may be held stationary to avoid motion artifacts during image acquisition. The vacuum features of the invention may also be used to mitigate motion artifacts. Should motion occur, scans may be automatically aligned to the statistically-most likely position given the data acquired. Furthermore, holding the patient 10 stationary and compensating for movement removes the need for invasive fiducial bone markers or high-error skin markers. In some embodiments, B-mode images may also be processed from the gathered data (Block 154) for subsequent visualization and overlain with the anatomical contours, as described in more detail below. In the case where a joint is being imaged, when the RF signal 142 (and if desired B-mode image) acquisition is complete for a first degree of flexion, the patient's joint may be moved to another degree of flexion and another reflected RF signal acquired (Block 156). Again, if desired, the B-mode image may also be acquired (Block 158). The user then determines whether acquisition is complete or whether additional data is required (Block 160). That is, if visualization of a desired surface of one or more anatomical features is occluded ("NO" branch of decision block 160), then the method returns to acquire additional data at another degree of flexion (Block 156). If the desired surfaces are sufficiently visible ("YES" branch of decision block 160), then the method 150 continues. Resultant RF signal profiles, anatomical models, bone models, bone contours, and so forth may be displayed on the monitor 26 during and after the model reconstruction.

Figure 17A:
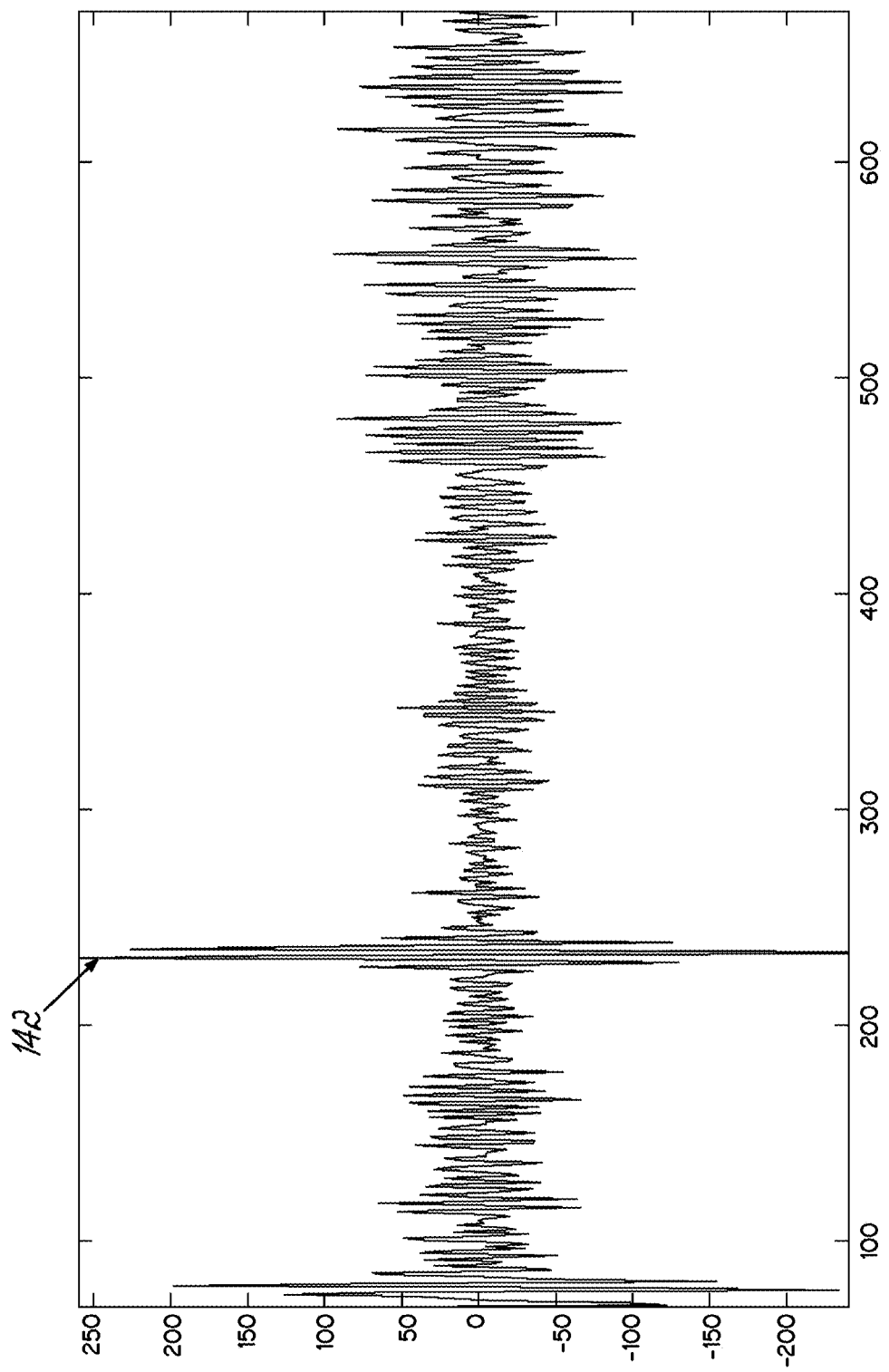
FIG. 17A is an example of a raw RF signal as acquired by one sensor of the sensor array of an ultrasound probe.

After all data and RF signal acquisition is complete, the computer 22 is operated to automatically isolate that portion of the RF signal, i.e., the bone contour, from each of the plurality of RF signals. In that regard, the computer 22 may sample the echoes comprising the RF signals to extract a bone contour for generating a 3-D point cloud 165 (FIG. 17B) (Block 164). More specifically, and with reference now to FIGS. 17A-17E, one method 164 of extracting the bone contours from each of the RF signal 142 is shown. FIG. 17A illustrates one exemplary, raw RF signal 142 as acquired by one or more sensors 52, 86, 92 of the cover 12. Each acquired raw, RF signal includes a number of echoes 162, wherein the echoes 162 may be isolated, partially overlapping, or fully overlapping. Each of the plurality of echoes originates from a reflection of at least a portion of the ultrasound energy at an interface between two tissues having different reflection and/or attenuation coefficients, as described in greater detail below.

Figure 17B:
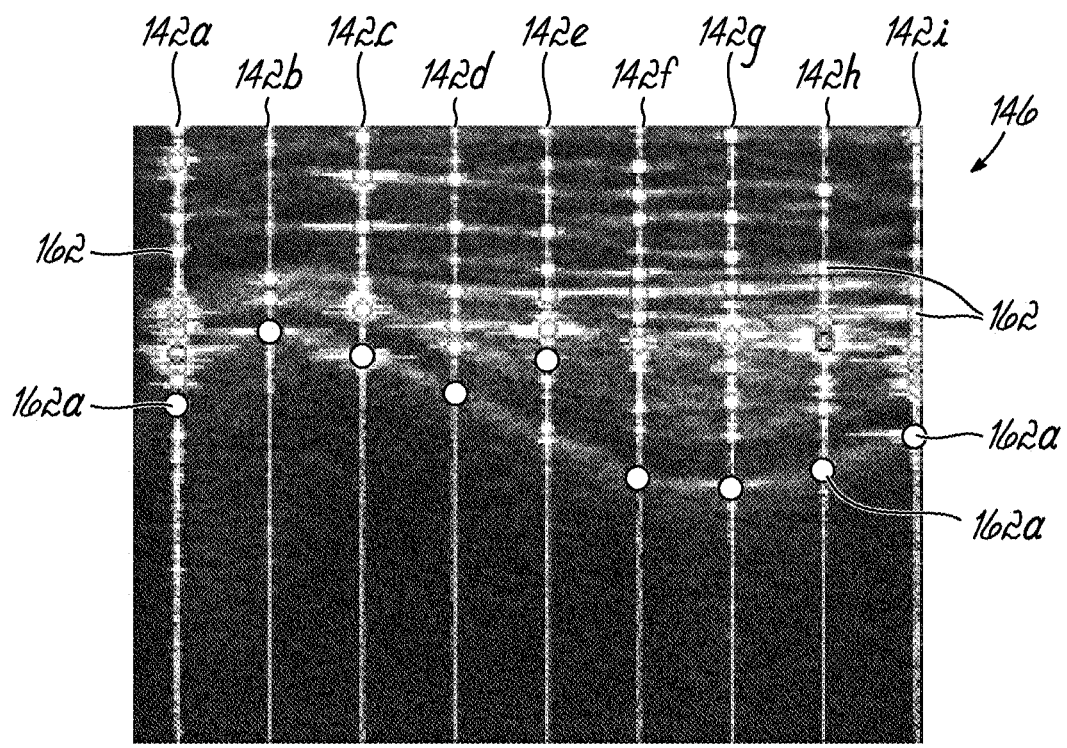
FIG. 17B illustrates RF signals overlaid on a B-mode ultrasound image.
Figure 17C:
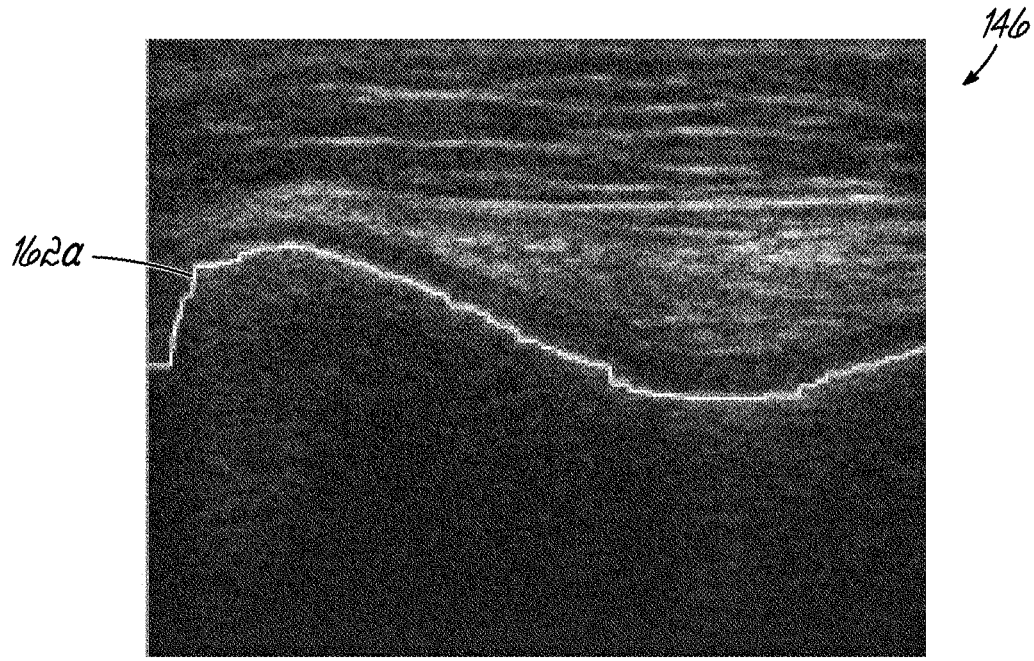
FIG. 17C is the ultrasound frame of a B-mode ultrasound image with a bone echo contour identified.
Figure 17D:
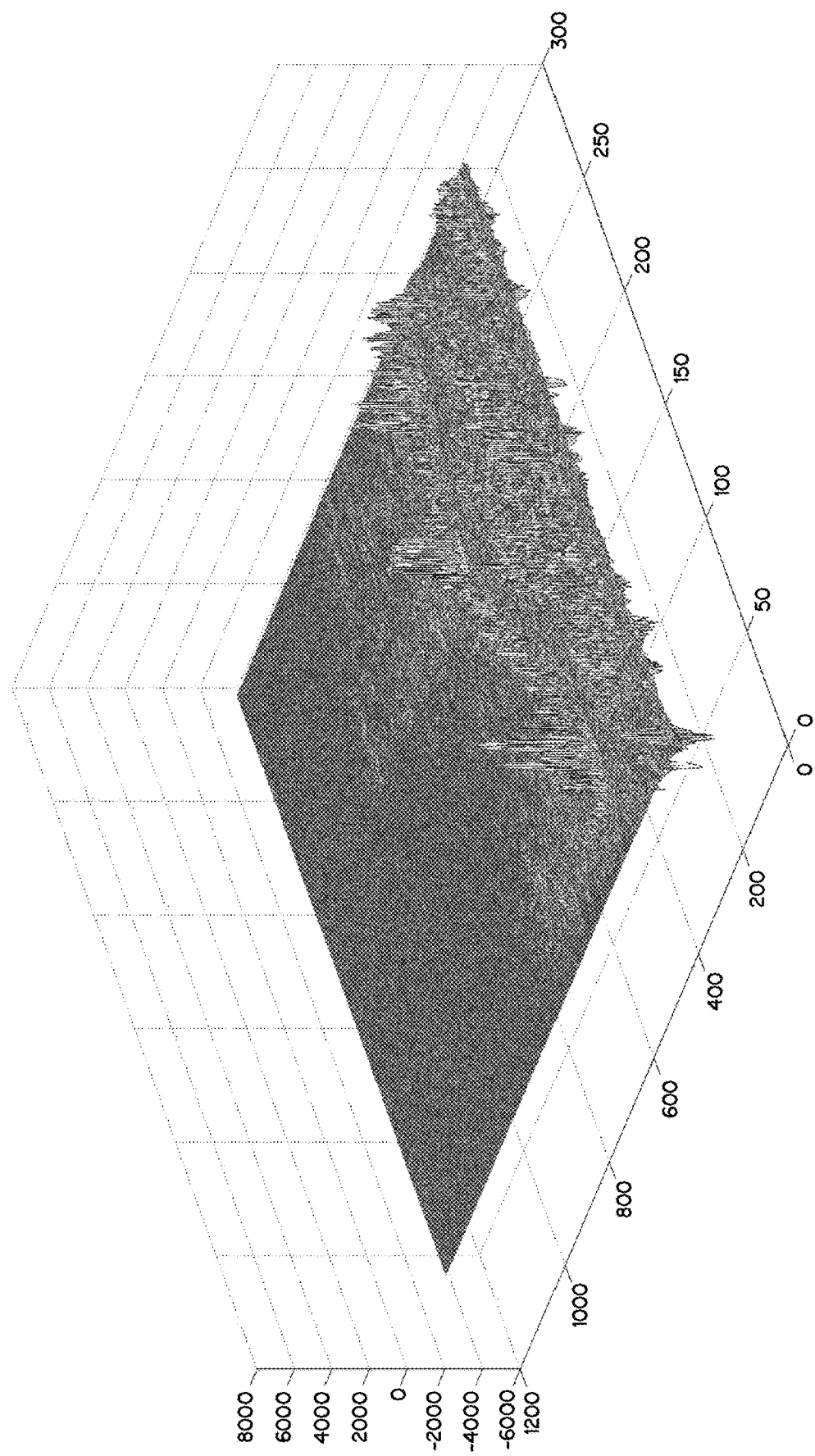
FIG. 17D is a 3-D rendering of the RF signals acquired in a data frame, which is shown in the B-mode image format in FIG. 17C.
Figure 17E:
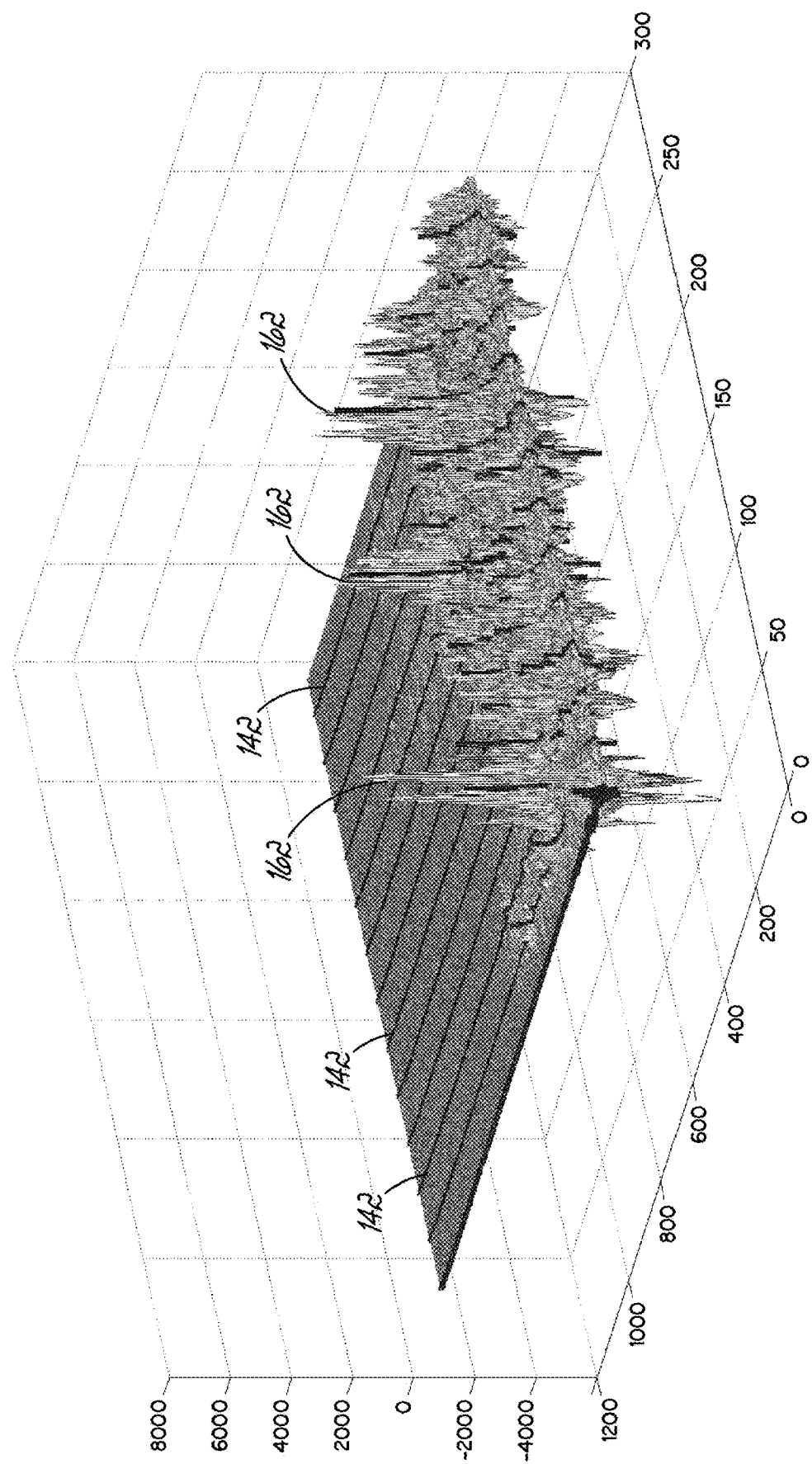
FIG. 17E is another 3-D rendering of an ultrasound frame with select ones of the RF signals delineated.

FIGS. 17B and 17C illustrate an ultrasound frame 146 having select ones of the raw RF signals 142 with some echoes 162 identified. FIGS. 17D and 17E are 3-D renderings of 2D images taken from an ultrasound frame 146 with select ones of the RF signals 142 identified in FIG. 17E.

Figure 18:
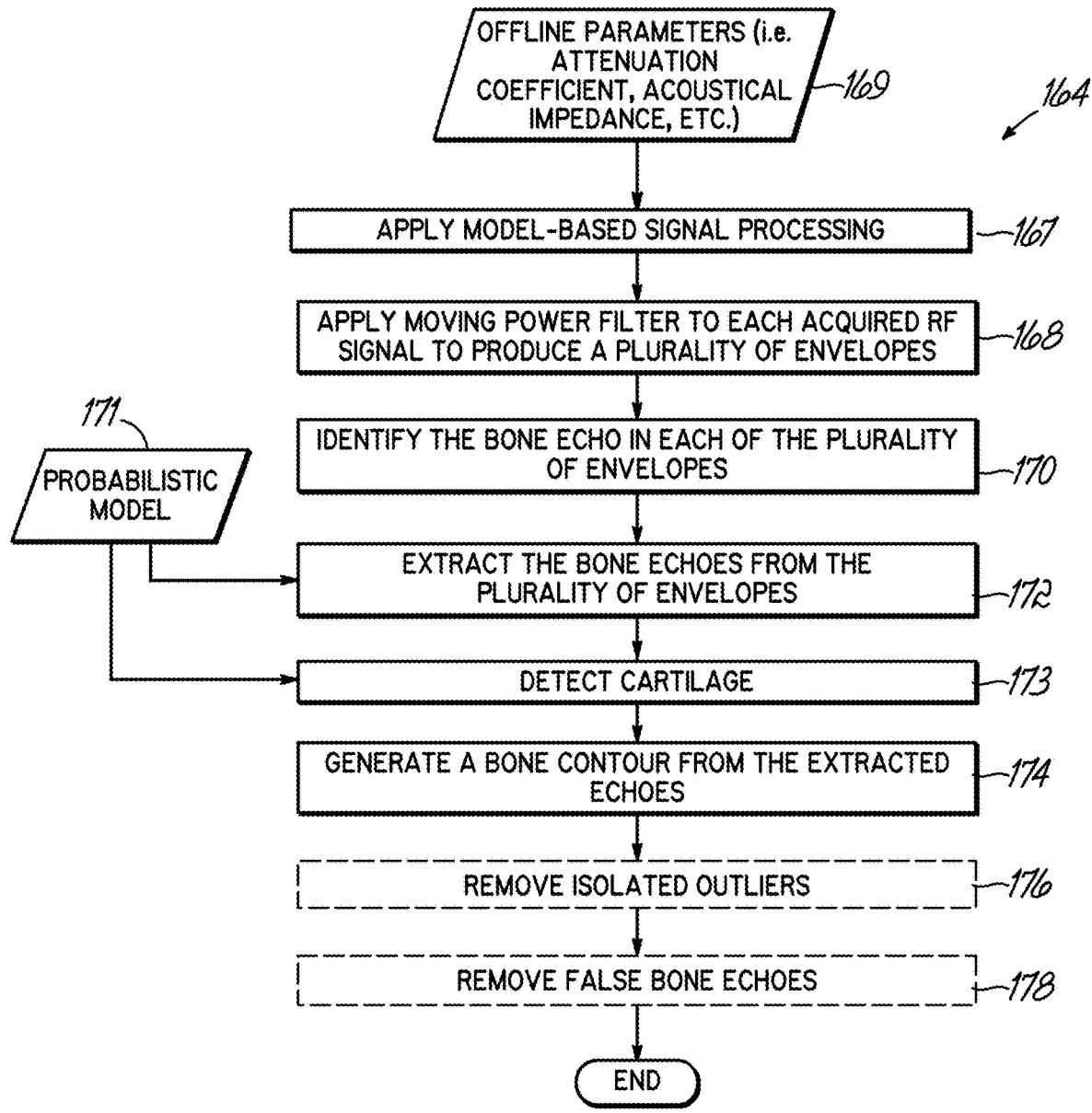
FIG. 18 is a flow chart illustrating one exemplary method of identifying and extracting an echo from the A-mode ultrasound RF signal.
Figure 19A:
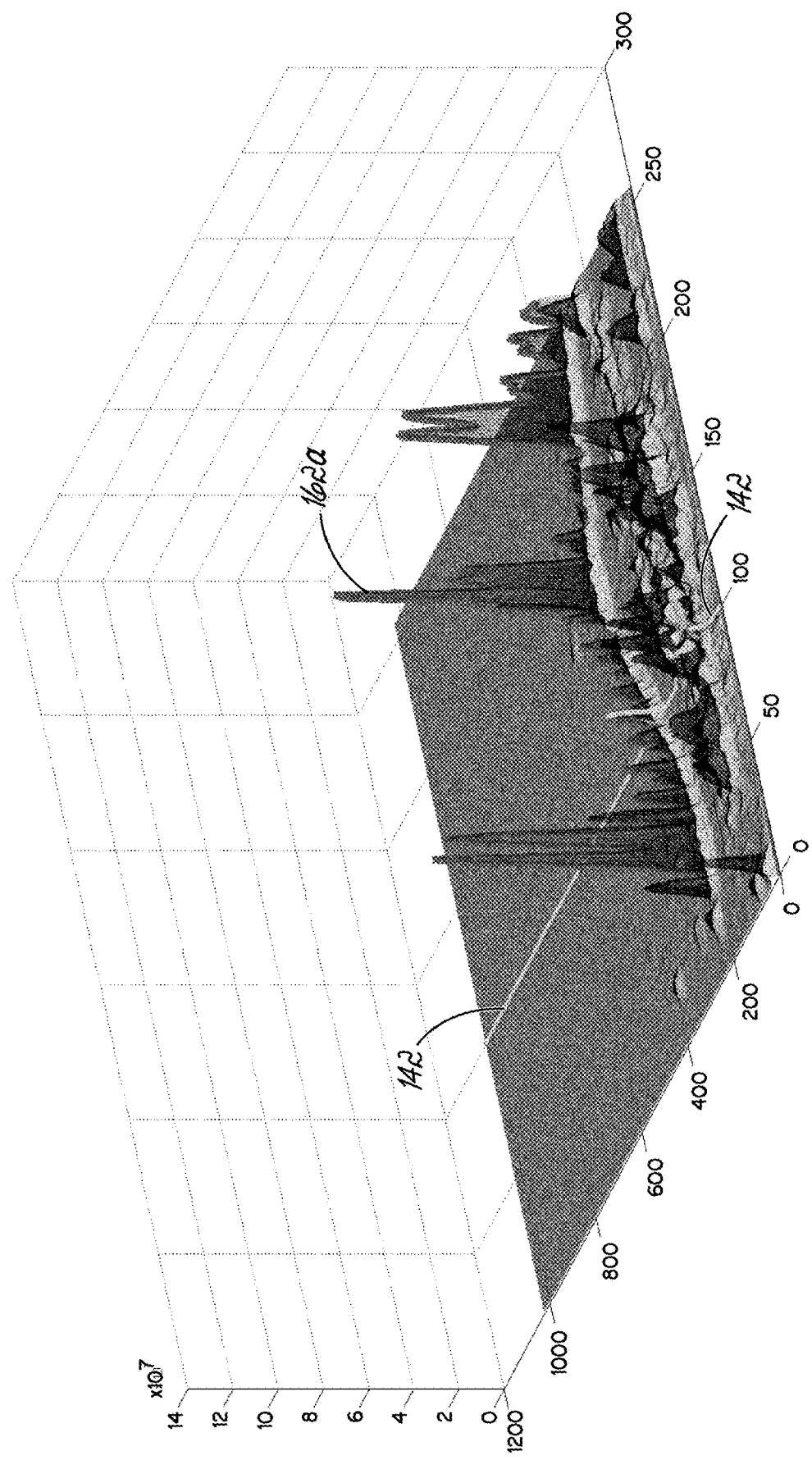
FIG. 19A is a 3-D rendering of an ultrasound frame after envelope detection.
Figure 19B:
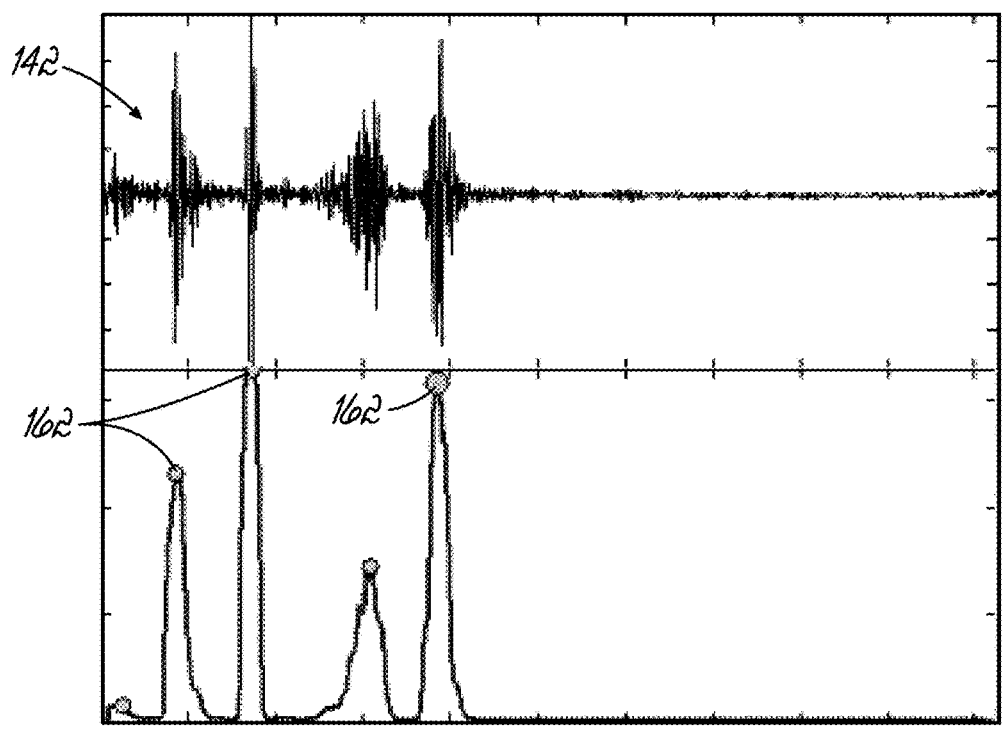
FIGS. 19B-19E respectively illustrate four exemplary envelopes of the sampled A-mode ultrasound RF signal, with the echoes identified in each envelope.
Figure 19C:
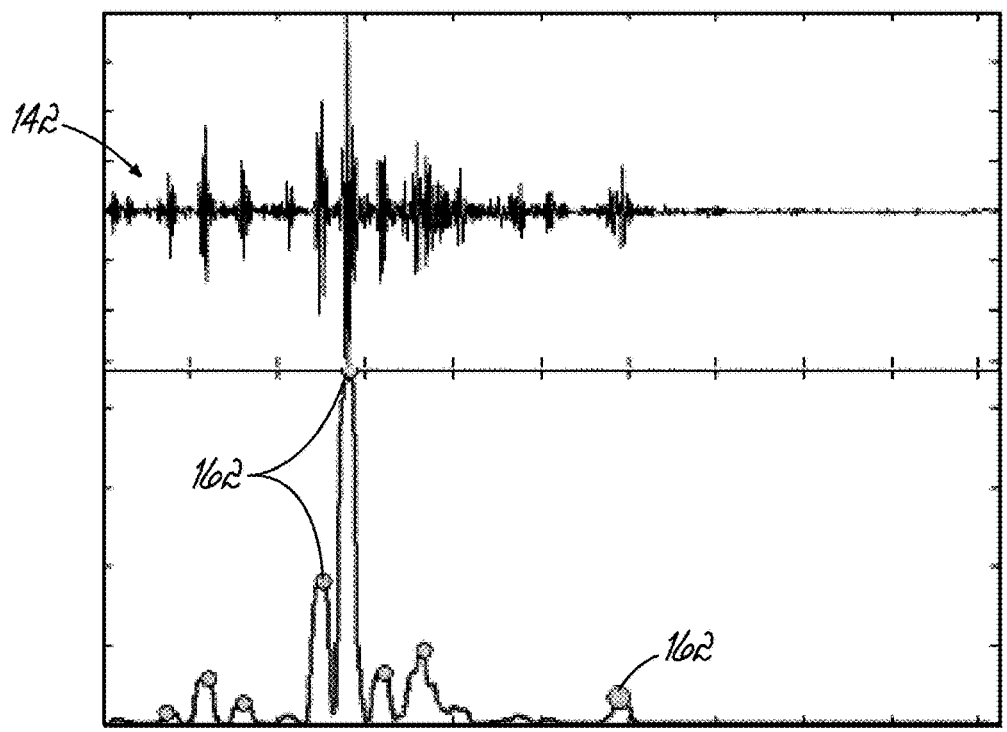
Figure 19D:
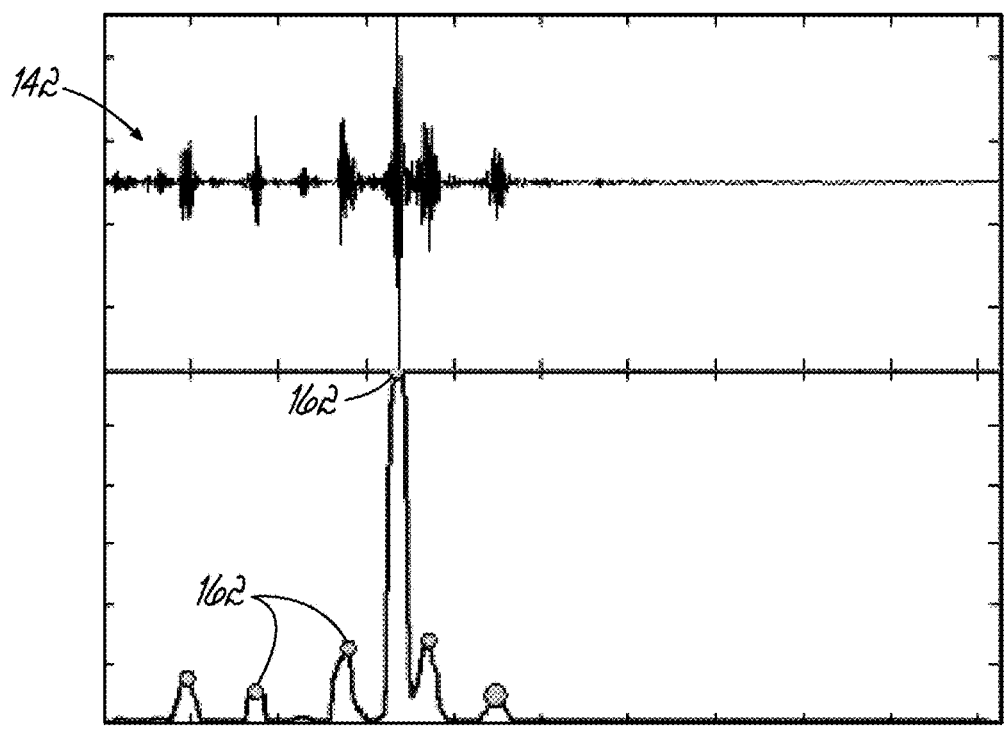
Figure 19E:
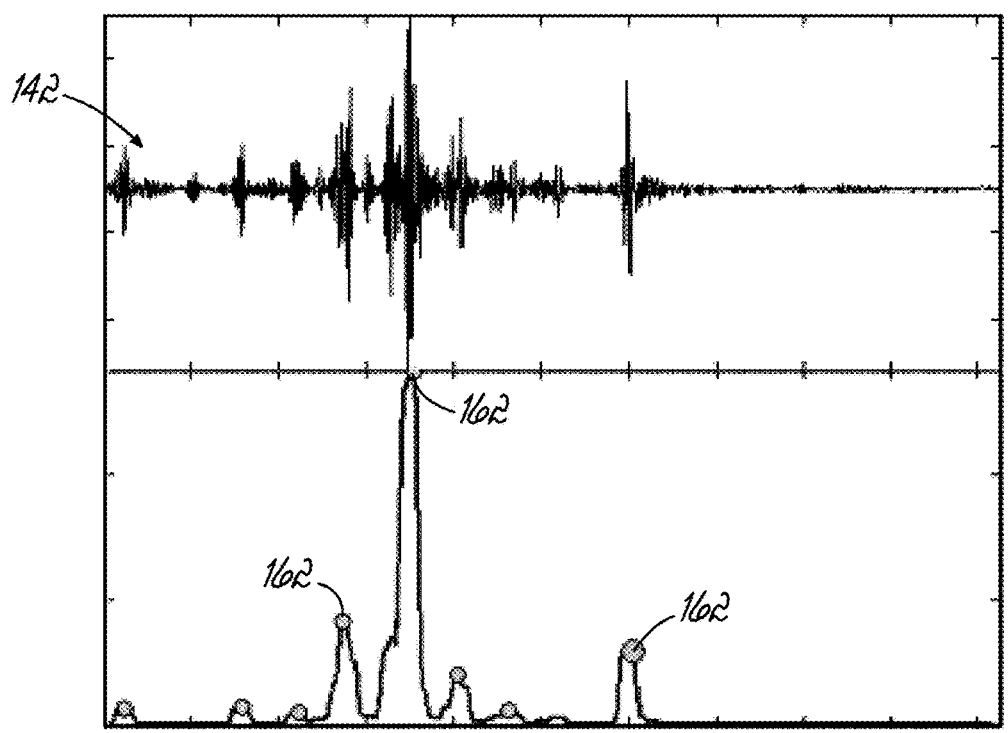

Referring now to FIG. 18, the method of extracting the bone contour 162*a* (FIG. 19A) begins with a model-based signal processing approach incorporating a priori knowledge of an underlying physical problem into a signal processing scheme. In this way, the computer 22 may process the RF signal 142 and remove some preliminary noise based on an estimated, or anticipated, result. For example, with ultrasound signal acquisition, the physical problem is represented by the governing waveform equation, such as described in VARSLOT T, et al., "Computer Simulation of Forward Wave Propagation in Soft Tissue," *IEEE Transactions on Ultrasonics, Ferroelectrics, and Frequency Control*, 1473-1482:52(9), September 2005, which paper is incorporated by reference herein in its entirety. The wave equation describes the propagation behavior of the ultrasonic wave in a heterogeneous medium. The solution to the wave equation may be represented as a state-space model-based processing scheme, such as described in CHEN Z, et al., "Bayesian Filtering: From Kalman Filters to Particle Filters, and Beyond," *Statistics*, 1-69, retrieved from http://citeseerx-.ist.psu.edu/viewdoc/download?doi=10.1.1.107.7415&rep=rep1&type=pdf, accessed August 2011, which paper is incorporated by reference herein in its entirety. In accordance with one embodiment of the present invention, a general solution to the model-based ultrasound wave estimator problem is developed using Bayesian estimators (e.g., maximum a posteriori), which leads to a nonlinear model-based design.

The model-based signal processing of the RF signal 142 begins with enhancing the RF signal by applying the model-based signal processing (here, the Bayesian estimator) (Block 167). To apply the Bayesian estimator, offline measurements are first collected from phantoms, cadavers, and/ or simulated tissues to estimate certain unknown parameters, for example, an attenuation coefficient (i.e., absorption and scattering) and an acoustic impedance (i.e., density, porosity, compressibility), in a manner generally described in VARSLOT T (refer above). The offline measurements (Block 169) are input into the Bayesian estimator and the unknown parameters are estimated as follows:

$$z = h(x) + v \quad (1)$$

$$P(t) = e^{(-\beta t/2)} \cdot \cos(2\pi f_0 \cdot t) \quad (2)$$

Where h is the measurement function that models the system and v is the noise and modeling error. In modeling the system, the parameter, x, that best fits the measurement, z, is determined. For example, the data fitting process may find an estimate of $\hat{x}$ that best fits the measurement of z by minimizing some error norm, $\|\varepsilon\|$, of the residual, where:

$$\varepsilon = z - h(\hat{x}) \quad (3)$$

For ultrasound modeling, the input signal, z, is the raw RF signal from the offline measurements, the estimate $h(\hat{x})$ is based on the state space model with known parameters of the offline measurements (i.e., density, etc.). The error, v, may encompass noise, unknown parameters, and modeling errors in an effort to reduce the effect of v by minimizing the residuals and identifying the unknown parameters form repeated measurements. Weighting the last echo within a scan line by approximately 99%, as bone, is one example of using likelihood in a Bayesian framework. A Kalman filter may alternatively be used, which is a special case of the recursive Bayesian estimation, in which the signal is assumed to be linear and have a Gaussian distribution.

It would be readily appreciated that the illustrative use of the Bayesian model here is not limiting. Rather, other model-based processing algorithms or probabilistic signal processing methods may be used within the spirit of the present invention.

With the model-based signal processing complete, the RF signal 142 is then transformed into a plurality of envelopes to extract the individual echoes 162 existing in the RF signal 142. Each envelope is determined by applying a moving power filter to each RF signal 142 (Block 168) or other suitable envelope detection algorithm. The moving power filter may be comprised of a moving kernel of length that is equal to the average length of an individual ultrasound echo 162. With each iteration of the moving kernel, the power of the RF signal 142 at the instant kernel position is calculated. One exemplary kernel length may be 20 samples; however, other lengths may also be used. The value of the RF signal 142 represents the value of the signal envelope at that position of the RF signal 142. Given a discrete-time signal, X, having a length, N, each envelope, Y, using a moving power filter having length, L, is defined by:

$$Y_k = \sum_{i=k-\frac{L}{2}}^{k+\frac{L}{2}} X_i^2 \; \forall \, k \in \left[\frac{L}{2}, N - \frac{L}{2} - 1\right] \quad (4)$$

In some embodiments, this and subsequent equations use a one-sided filter of varying length for the special cases of the samples before the L/2 sample (left-sided filter), and after the $$N - \frac{L}{2} - 1$$

sample (right-sided filter).

Each envelope produced by the moving power filter, as shown in FIG. 17B, includes a plurality of local peaks (identified in FIG. 17B as enlarged dots at the intersection of each envelope with an echo 162). Each local peak is a clear representation of the individual echoes 162 existing in the acquired RF signal 142 for the various tissue interfaces. As an example of such process, FIGS. 19A-19D more clearly illustrate the RF signal 142 (top in each figure) at four iterations of the kernel of the moving power filter as well as the corresponding envelope (bottom in each figure). Individual echoes 162 in each envelope are again identified with an enlarged dot.

Of the plurality of echoes 162 in the RF signal 142, one echo 162 is of particular interest, e.g., the echo corresponding to the bone-soft tissue interface. This bone echo 162*a* is generated by the reflection of the ultrasound energy at the surface of the scanned bone. More particularly, the soft tissue-bone interface is characterized by a high reflection coefficient of 43%, which means that 43% of the ultrasound energy reaching the surface of the bone is reflected back to the sensors 52, 86, 92 of the cover 12. This high reflectivity gives bone the characteristic hyper-echoic appearance in an ultrasound image.

Bone is also characterized by a high attenuation coefficient of the applied RF signal (6.9 db/cm/mHz for trabecular bone and 9.94 db/cm/mHz for cortical bone). At high frequencies, such as those used in musculoskeletal imaging (that is, in the range of 7-14 MHz), the attenuation of bone becomes very high and the ultrasound energy ends at the surface of the bone. Therefore, an echo 162a corresponding to the soft-tissue-bone interface is typically the last echo 162a in the RF signal 142. The bone echo 162a is identified by selecting the last echo having a normalized envelope amplitude (with respect to a maximum value existing in the envelope) above a preset threshold (Block 170).

The bone echoes 162a are then extracted from each frame 146 (Block 172) and used to generate the bone contour existing in that RF signal 142, as shown in FIG. 17C (Block 174). In extracting the bone echoes, a probabilistic model (Block 171) may be input and applied to the RF signals 142 of each frame 146. The probabilistic model (Block 171) may further be used in detecting cartilage within the envelopes of the RF signals 142 (Block 173). While the probabilistic signal processing method may include the Bayesian estimator described previously, in still other embodiments, the signal processing may be a maximum likelihood ratio, neural network, or a support vector machine ("SVM"), for example, the latter of which is further described below.

Prior to implementing the SVM, the SVM may be trained to detect cartilage in RF signals. One such way of training the SVM includes information acquired from a database comprising of MRI images and/or RF ultrasound images to train the SVM to distinguish between echoes associated with cartilage from the RF signals 142, and from within the noise or in ambiguous soft tissue echoes. In constructing the database in accordance with one embodiment, bone structures from multiple patient's are imaged using both MRI and ultrasound. A volumetric MRI image of each bone structure is reconstructed, processed, and the cartilage and the bone tissues are identified and segmented. The segmented volumetric MRI image is then registered with a corresponding segmented ultrasound image (wherein bone tissue is identified). The registration provides a transformation matrix that may then be used to register the raw RF signals 142 with a reconstructed MRI surface model.

After the raw RF signals 142 are registered with the reconstructed MRI surface model, spatial information from the volumetric MRI images with respect to the cartilage tissue may be used to determine the location of a cartilage interface on the raw RF signal 142 over the articulating surfaces of the bone structure.

The database of all bone structure image pairs (MRI and ultrasound) is then used to train the SVM. Generally, the training includes loading all raw RF signals, as well as the location of the bone-cartilage interface of each respective RF signal. The SVM may then determine the location of the cartilage interface in an unknown, input raw RF signal. If desired, a user may chose from one or more kernels to maximize a classification rate of the SVM.

In use, the trained SVM receives a reconstructed bone structure image of a new patient as well as the raw RF signals. The SVM returns the cartilage location on the RF signal data, which may be used, along with tracking information from the sensor controller 54 to generate 3-D coordinates for each point on the cartilage interface. The 3-D coordinates may be triangulated and interpolated to form a complete cartilage surface.

With continued reference to FIG. 18, the resultant bone contours may be noisy and require filtering to remove echoes 162 that may be falsely detected as the bone echo 162a. Falsely detected echoes 162 may originate from one of at least two sources: (1) an isolated outlier echoes and (2) a false bone echoes. Furthermore, some images may not include a bone echo 162a; therefore any detected echo 162 is noise and should be filtered out. Therefore, proper determination of the preset threshold or filtering algorithm may prevent the false selection of a falsely detected echo 162.

Isolated outliers are those echoes 162 in the RF signal 142 that correspond to a tissue interface that is not the soft-tissue-bone interface. Selection of the isolated outliers may occur when the criterion is set too high. If necessary, the isolated outliers may be removed (Block 176) by applying a median filter to the bone contour. That is, given a particular bone contour, X, having a length, N, with a median filter length, L, the median-filter contour, $Y_k$, is:

$$Y_k = \text{Median}\left[X_{k-\frac{L}{2}}, X_{k+\frac{L}{2}}\right] \forall k \in \left[\frac{L}{2}, N - \frac{L}{2} - 1\right] \quad (5)$$

False bone echoes are those echoes 162 resulting from noise or a scattering echo, which result in a detected bone contour in a position where no bone contour exists. The false bone echoes may occur when an area that does not contain a bone is scanned, the ultrasound sensor 52, 86, 92 is not oriented substantially perpendicular with respect to the bone surface, the bone lies deeper than a selected scanning depth, the bone lies within the selected scanning depth but its echo is highly attenuated by the soft tissue overlying the bone, or a combination of the same. Selection of the false bone echoes may occur when the preset threshold is too low.

Frames 146 containing false bone echoes should be removed. One such method of removing the false bone echoes (Block 178) may include applying a continuity criteria. That is, because the surface of the bone has a regular shape, the bone contour, in the two-dimensions of the ultrasound image, should be continuous and smooth. A false bone echo will create a non-continuity, and exhibits a high degree of irregularity with respect to the bone contour.

One manner of filtering out false bone echoes is to apply a moving standard deviation filter; however, other filtering methods may also be used. For example, given the bone contour, X, having a length, N, with a median filter length, L, the standard deviation filter contour:

$$Y_k = \sqrt{\frac{1}{L-1} \sum_{i=k-\frac{L}{2}}^{i=k-\frac{L}{2}} (X_i - \overline{X})^2} \quad \forall k \in \left[\frac{L}{2}, N - \frac{L}{2} - 1\right] \quad (6)$$

Where $Y_k$ is the local standard deviation of the bone contour, which is a measure of the regularity and continuity of the bone contour. Segments of the bone contour including a false bone echo are characterized by a higher degree of irregularity and have a high $Y_k$ value. On the other hand, segments of the bone contour including only echoes resulting from the surface of the bone are characterized by high degree regularity and have a low $Y_k$ value. A resultant bone contour 180, resulting from applying the moving median filter and the moving standard deviation filter, includes a full length contour of the entire surface of the bone, one or more partial contours of the entire surface, or contains no bone contour segments.

Figure 20A:
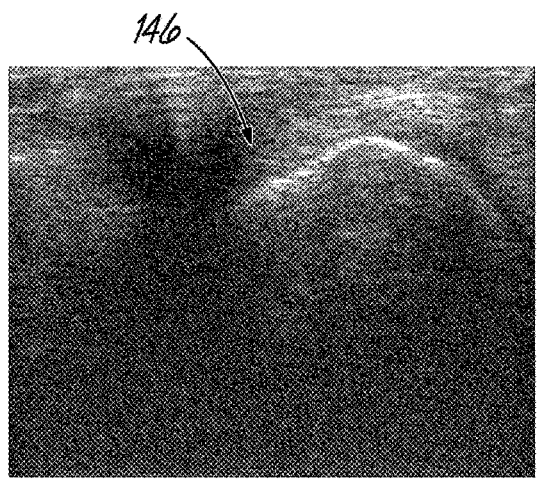
FIGS. 20A and 20D are B-mode ultrasound frames calculated from exemplary A-mode ultrasound RF signals.
Figure 20D:
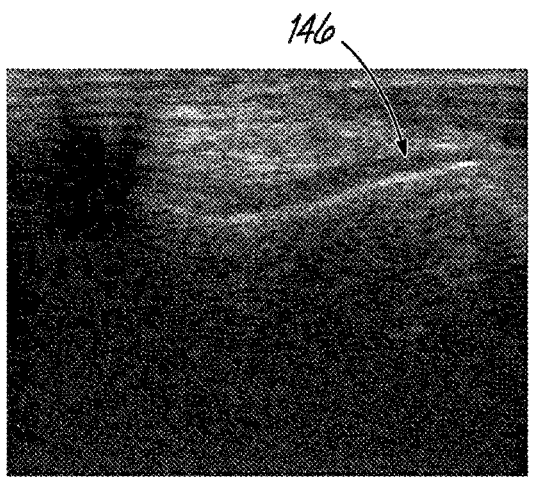
Figure 20B:
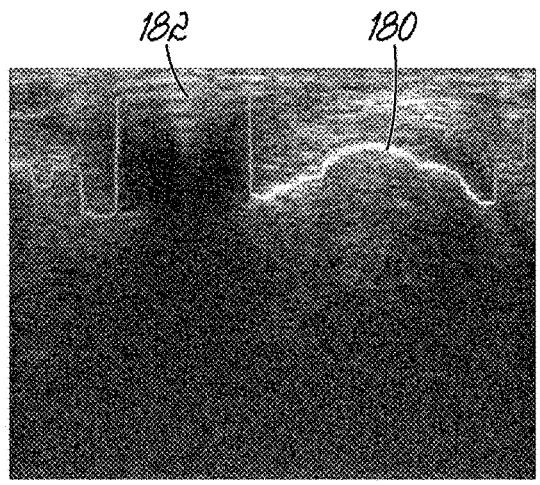
FIGS. 20B and 20E are ultrasound frames corresponding to FIGS. 20A and 20D, respectively, with a bone contour identified before noise removal and overlain on the B-mode image.
Figure 20E:
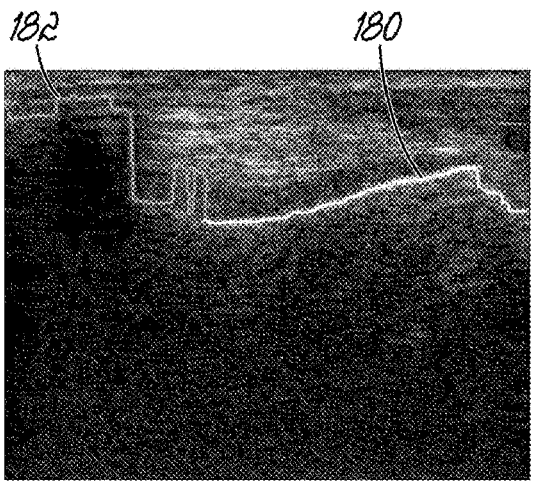
Figure 20C:
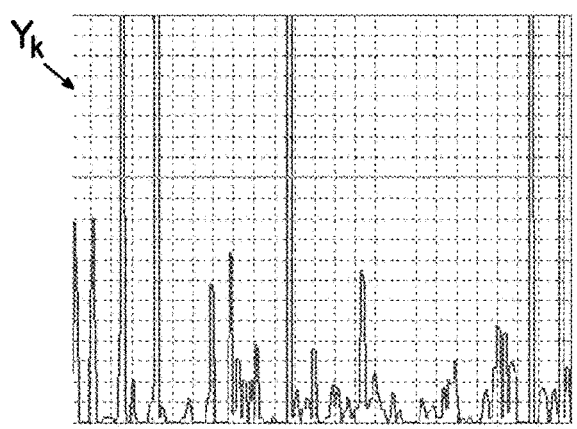
FIGS. 20C and 20F are plots of the local standard deviation of the bone contours of FIGS. 20B and 20E, respectively.
Figure 20F:
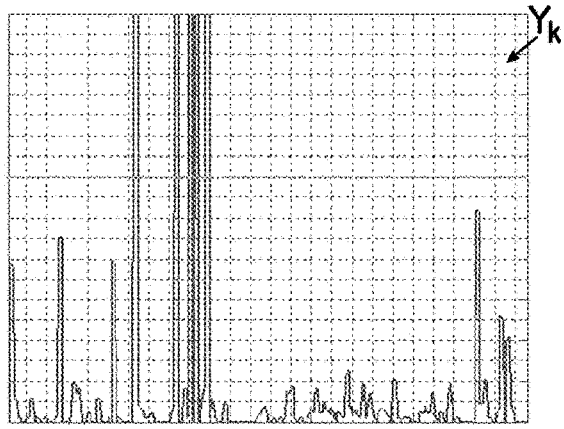
Figure 21A:
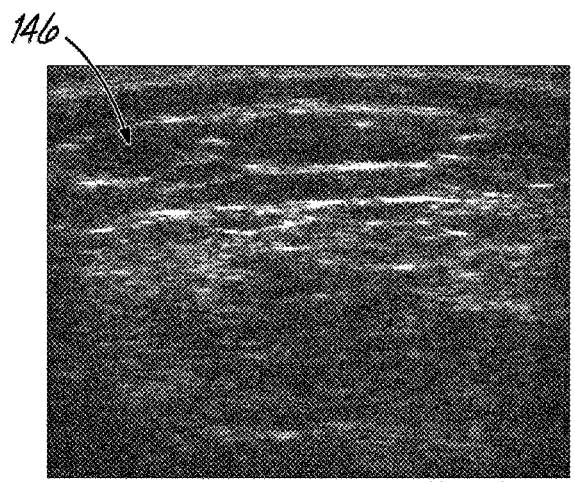
FIGS. 21A, 21D are ultrasound frames illustrating exemplary B-mode images constructed from A-mode ultrasound RF signals, and in which no bone tissue was scanned.
Figure 21D:
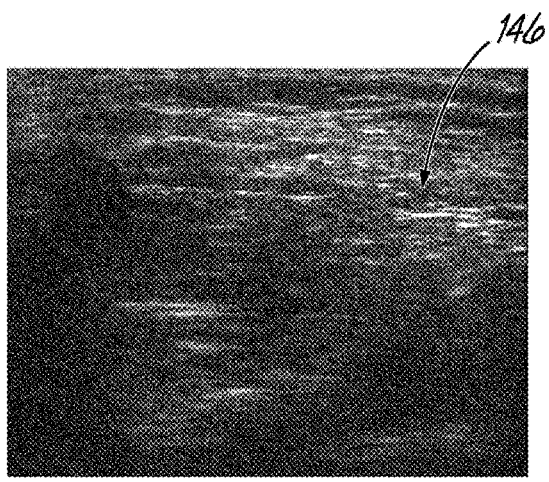
Figure 21B:
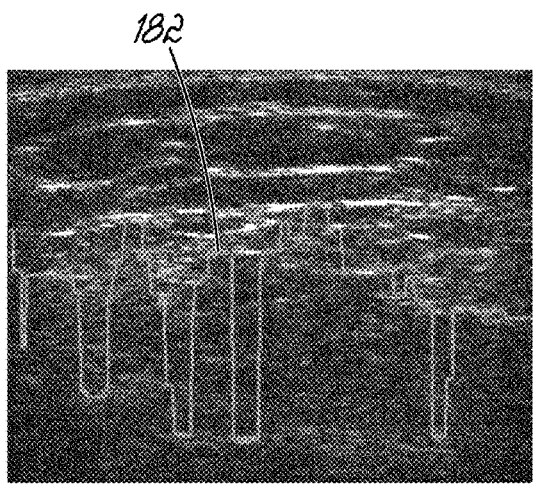
FIGS. 21B and 21E are ultrasound frames corresponding to FIGS. 21A and 21D, respectively, with the noisy false bone contours shown.
Figure 21E:
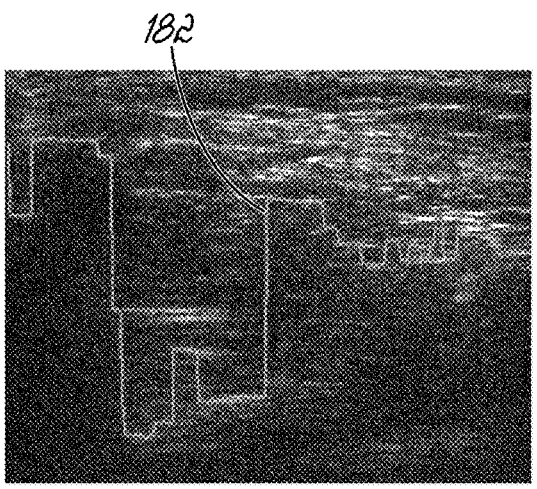
Figure 21C:
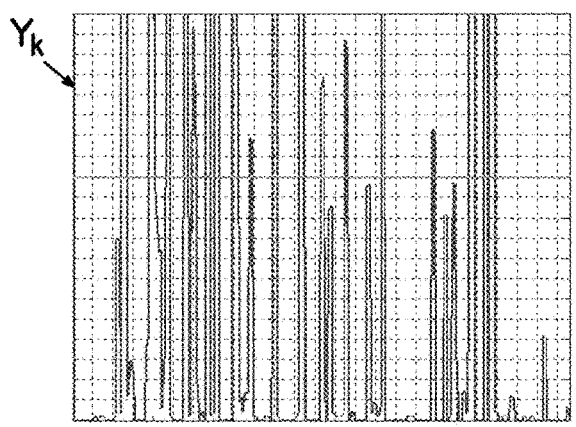
FIGS. 21C and 21F are plots of the local standard deviation of the last echoes of FIGS. 21B and 21E, respectively.
Figure 21F:
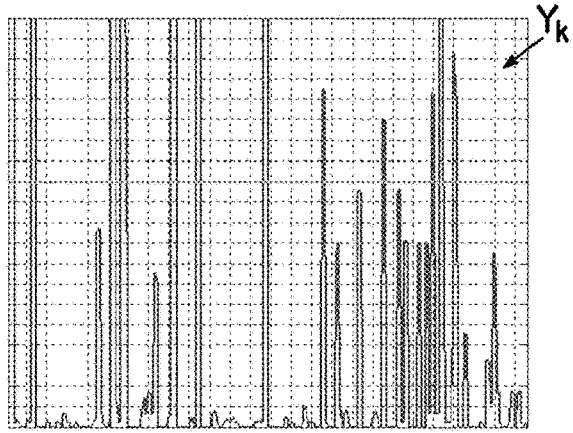

FIGS. 19A-19F and 20A-20F illustrate the resultant bone contour 180 that is selected from those segments of the extracted bone contour that satisfy two conditions: (1) the continuity criteria, having a local standard deviation value below selected standard deviation threshold, and (2) a minimum-length criteria, which avoids piecewise-smooth noise contour segments from being falsely detected as bone contour. In some exemplary embodiments, the length of the standard deviation filter may be set to 3 and the threshold set to 1.16 mm, which may correspond to 30 signal samples. Accordingly, FIGS. 20A and 20D illustrate two exemplary RF signals 142 with the resultant bone contours 180 extracted and filtered from the noise 182 (including isolated outliers and false body echoes), shown in FIGS. 20B and 20E, respectively. FIGS. 20C and 20F respectively illustrate the standard deviation, $Y_k$, calculated as provided in Equation 6 above. FIGS. 21A-21F are similar to FIGS. 20A-20F, but include two exemplary signals 142 in which no bone tissue was scanned.

With the bone contours isolated from each of the RF signals, the bone contours may now be transformed into a point cloud. For instance, returning now to FIG. 15, the resultant bone contours 180 may then undergo registration to construct a bone point cloud 194 representing the surface of at least a portion of each scanned bone (Block 186), which is described herein as a multiple step registration process. In one embodiment, the process is a two-step registration process. The registration step (Block 186) begins by transforming the resultant bone contour 180 from a 2D contour in the ultrasound frame into a 3-D contour in the world frame (Block 188). This transformation is applied to all resultant bone contours 180 extracted from all of the acquired RF signals 142.

To transform the resultant bone contour 180 into the 3-D contour, each detected bone echo 162a undergoes transformation into a 3-D point as follows:

$$d_{echo} = n_{echo} T_s C_{us} \qquad (7)$$

$$l_{echo} = L_{trans} \frac{n_{line}}{N_{lines}} \hat{u}_x \qquad (8)$$

$$P_{echo}^{OP} = P_{trans-origin} + d_{echo}\hat{u}_y + l_{echo}\hat{u}_x \qquad (9)$$

$$P_{echo}^{W} = H_{OP}^{W} P_{echo}^{OP} \qquad (10)$$

Where the variables are defined as follows:

| | |
|---|---|
| $d_{echo}$ | depth of the bone echo (cm) |
| $n_{echo}$ | sample index of the detected bone echo |
| $T_s$ | RF signal sampling period (sec/sample) |
| $C_{us}$ | speed of ultrasound in soft tissue (154 × 10³ cm/s) |
| $l_{echo}$ | distance from the $P_{trans-origin}$ (FIG. 2) of the transducer array 68 (FIG. 2) to the current scan line (cm) |
| $P_{echo}^{OP}$ | detected point on the bone surface represented in the local frame |
| $n_{line}$ | index of the scan line containing the bone echo in the image |
| $N_{lines}$ | number of scan lines in the image |
| $P_{echo}^{W}$ | detected surface of the bone relative to the world frame |
| $H_{OP}^{W}$ | homogeneous transformation between the local frame and the world frame, as described previously |
| $H_{OP}^{W}$ | dynamically obtained transformation that contains the position and orientation of the optical marker 86 (FIG. 2) |

Figure 16:
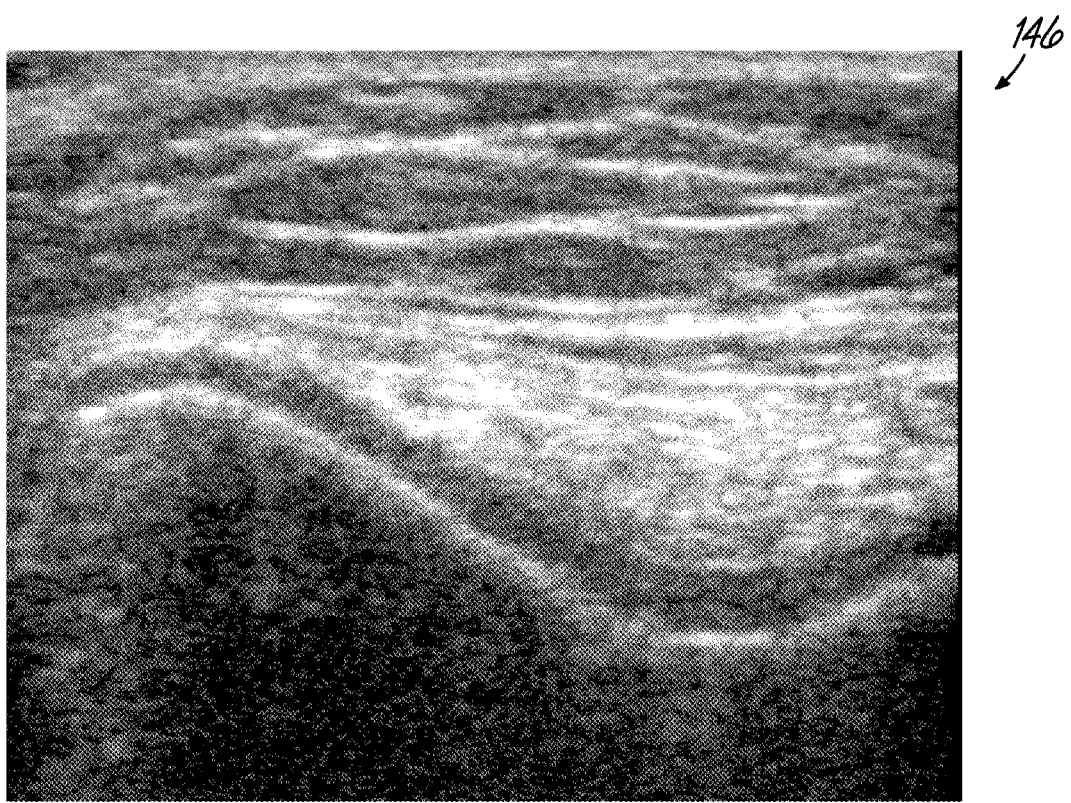
FIG. 16 is a B-mode ultrasound image which may optionally be shown from the A-mode ultrasound RF signal.

If so desired, an intermediate registration process may be performed between the resultant bone contour and a B-mode image, if acquired (Block 190). This registration step is performed for visualizing the resultant bone contour 180 with the B-mode image 146 (FIG. 16), which provides visual validation and feedback of the resultant bone contour 180 detection process, in real time, while the user is performing the scan. This visual validation may aid the user in determining whether acquisition is completed (Block 160), as described previously. More specifically, the resultant bone contour 180 is registered with the B-mode image by:

$$P_{echo}^{I} = (l_{echo} I_x, d_{echo} I_y) \qquad (11)$$

Where $I_x$ and $I_y$ denote the B-mode image resolution (pixels/cm) for the x- and y-axes respectively. $P_{echo}^{I}$ denotes the coordinates of the bone contour point relative to the ultrasound frame.

Figure 22:
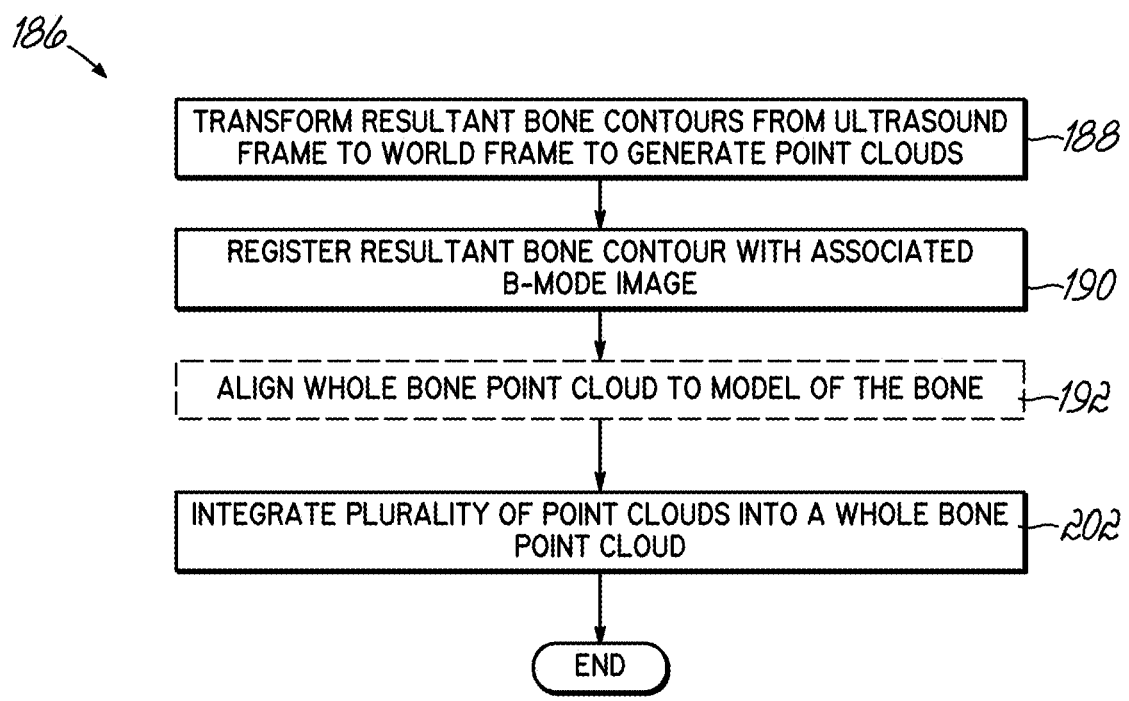
FIG. 22 is a flow chart illustrating one exemplary method of generating a bone point cloud from the isolated bone contours.
Figure 23B:
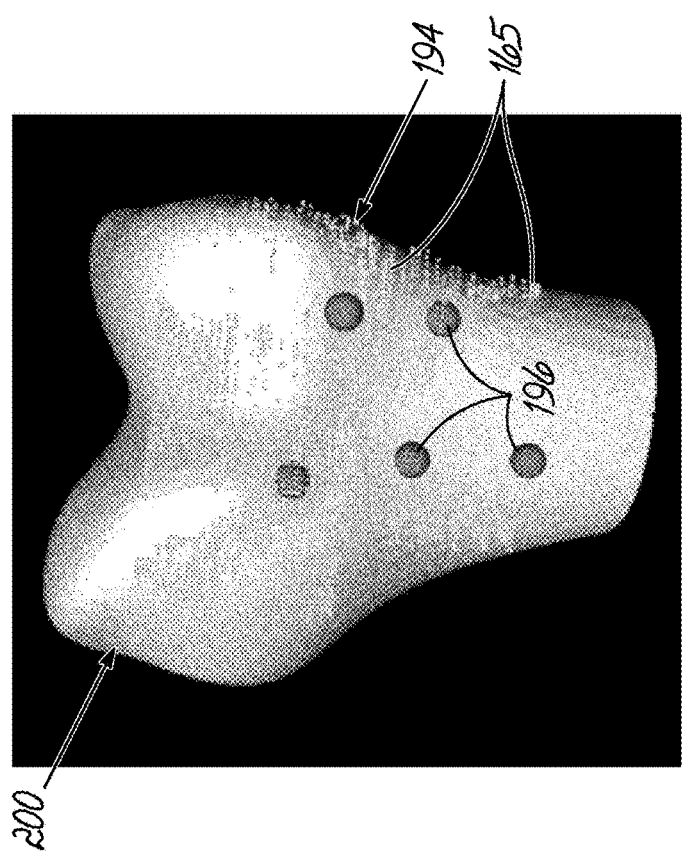
FIGS. 23B, 23D, 24B, and 24D are examples in which the bone point clouds of FIGS. 23A, 23C, 24A, and 24C, respectively, are aligned to a bone model.
Figure 23A:
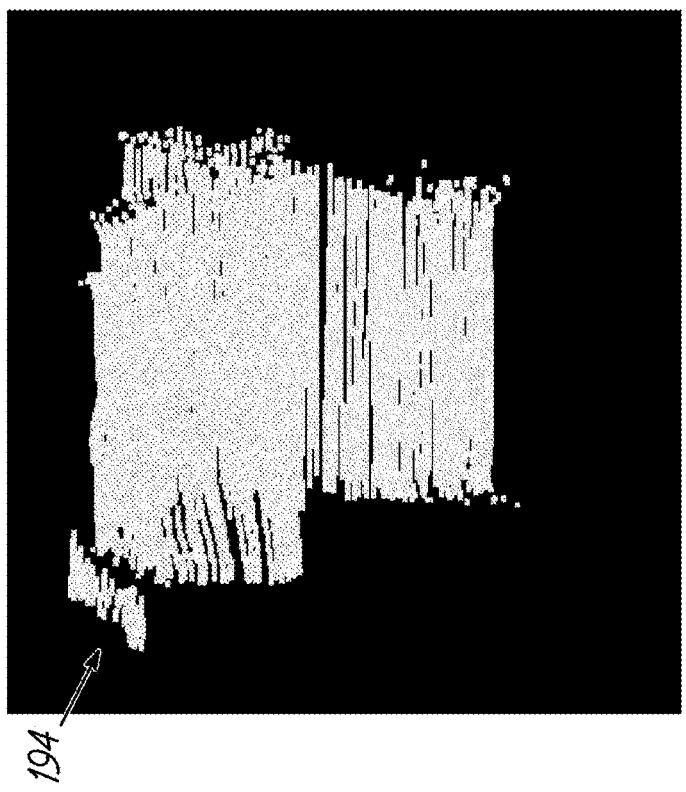
FIGS. 23A, 23C, 24A, and 24C are exemplary bone point clouds, generated in accordance with one embodiment of the present invention.
Figure 23D:
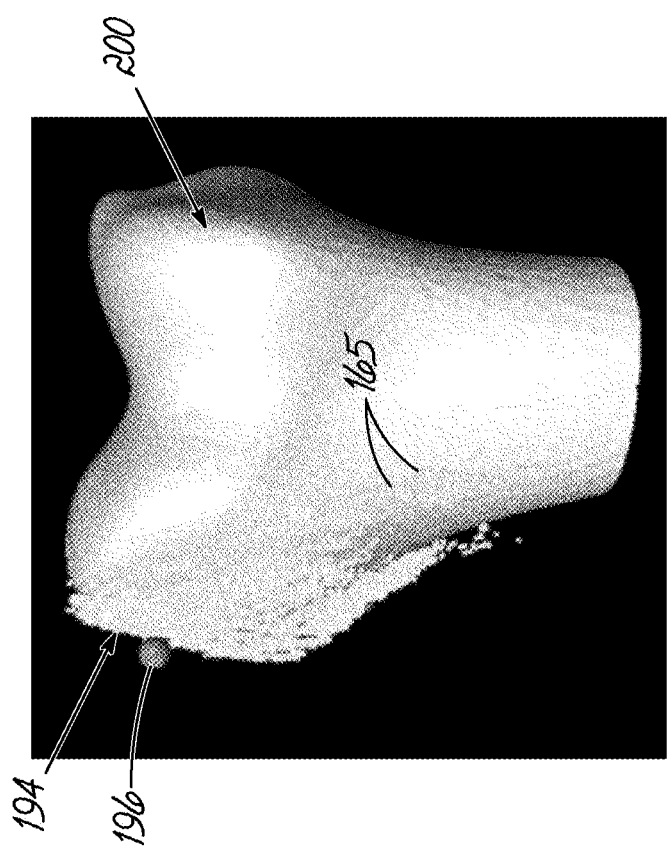
Figure 23C:
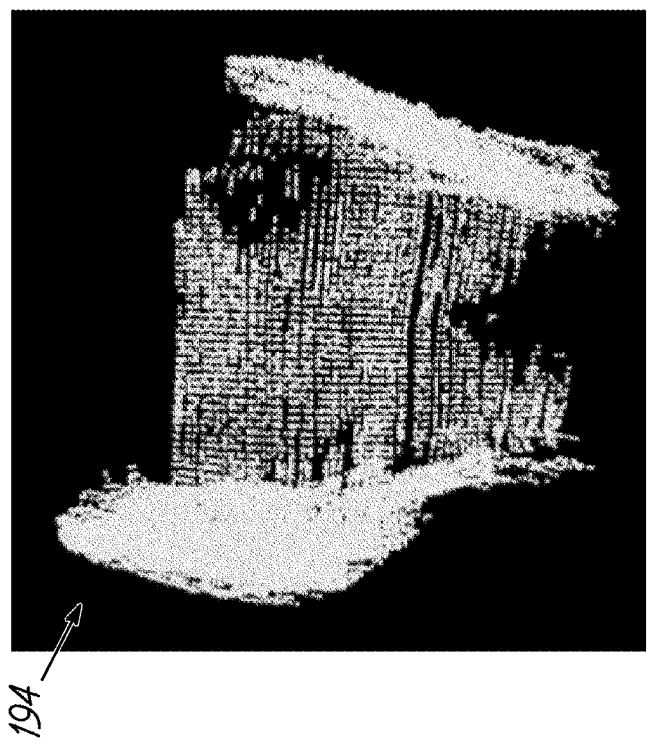
Figure 24B:
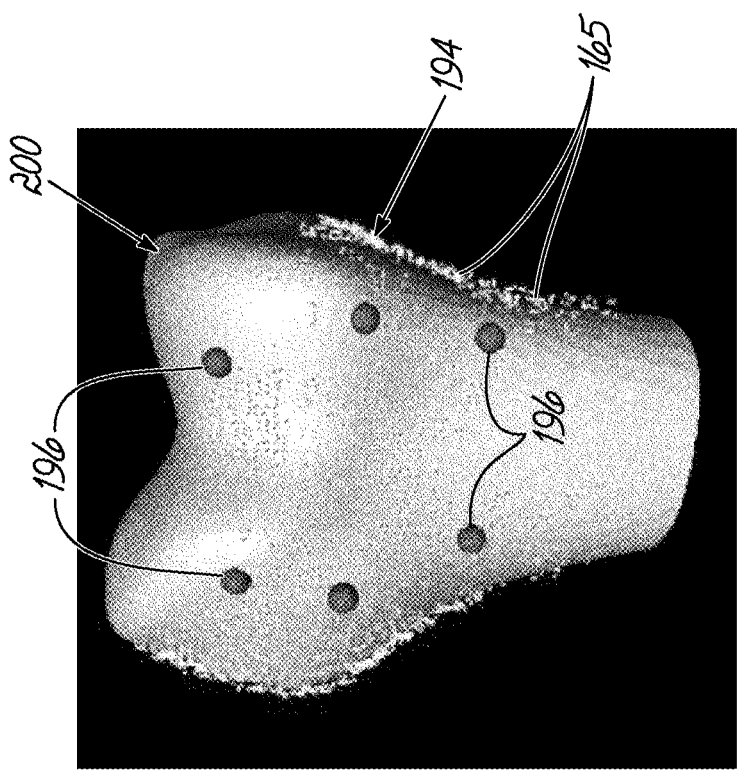
Figure 24A:
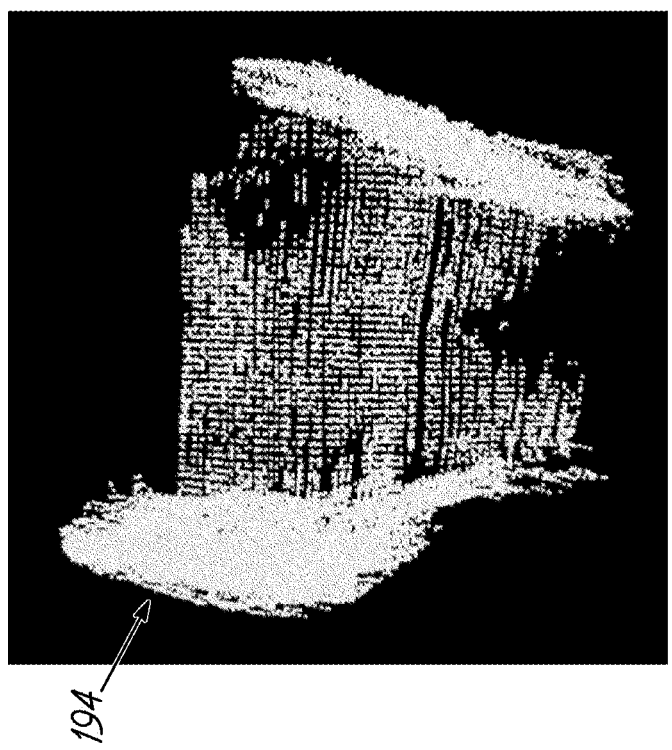
Figure 24D:
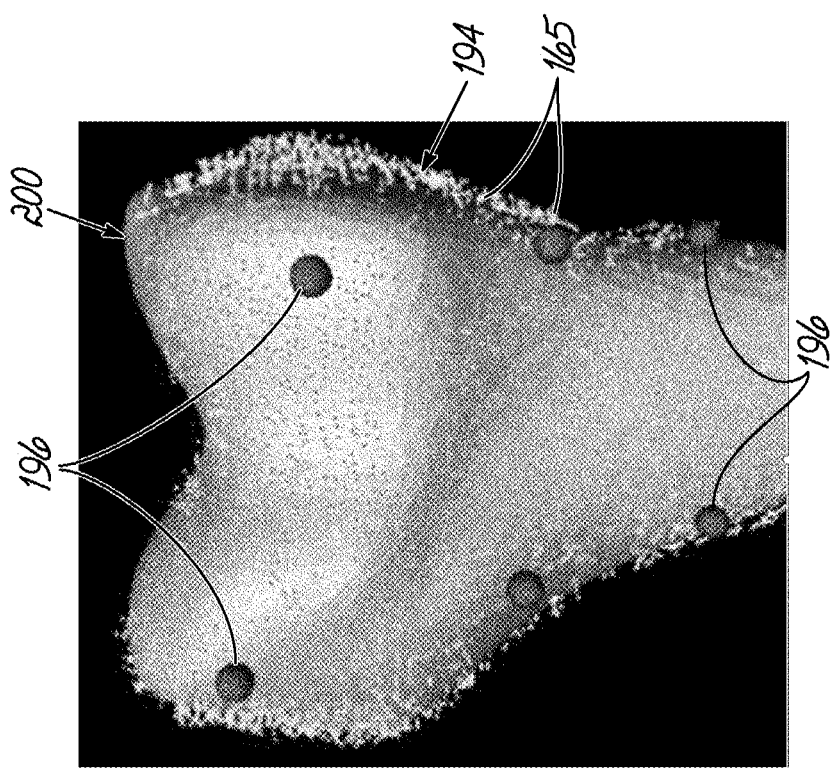
Figure 24C:
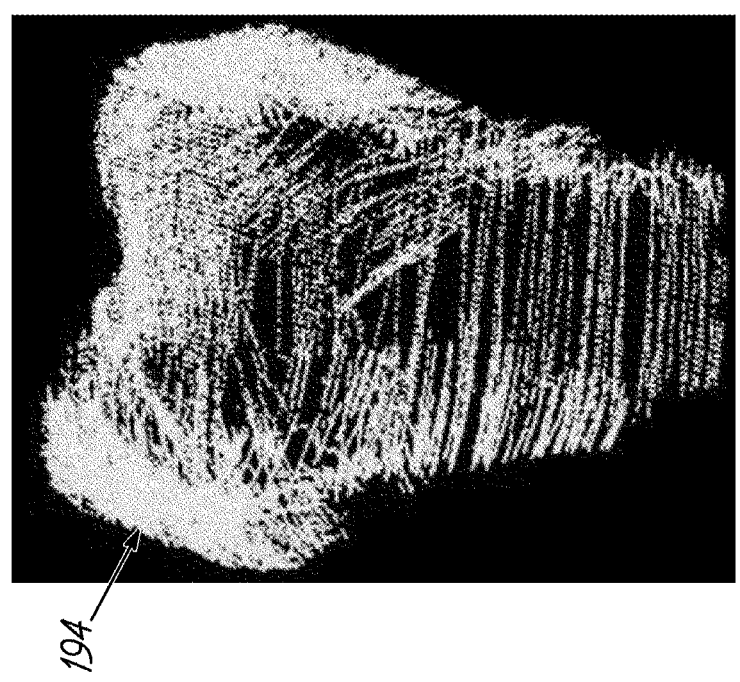

After the resultant bone contours 180 are transformed and, if desired, registered (Block 190) (FIG. 22), the plurality of point clouds 165 (FIG. 23B) are generated representing the surface of the bone. During the second registration process the plurality of point clouds 165 are integrated into a bone point cloud 194 representing the entire surface of the scanned bone.

To begin the second registration process, as shown in FIGS. 23A-23D, the plurality of point clouds 164 are initially aligned to a standardized model of the scanned bone, here a model bone 200, for example, by using 4-6 previously specified landmarks 196 (Block 192). More specifically, the user may identify the plurality of landmarks 196 on the model bone 200, which need not be identified with high accuracy. After this initial alignment, an iterative closest point ("ICP") alignment is performed to more accurately align the plurality of point clouds to the standardized model. If necessary, noise may be removed by thresholding for a distance between a respective point of the plurality of point clouds and the closest vertices in the model bone 200. However, alternative embodiments may use other filtering methods. For instance, an average distance plus one standard deviation may be used as the threshold. The process is repeated for each point cloud 165 of the plurality for the surface of the scanned bone. The now aligned point clouds 165 are then integrated into a single uniform point cloud 194 that represents the surface of the scanned bone (Block 202).

Figure 25:
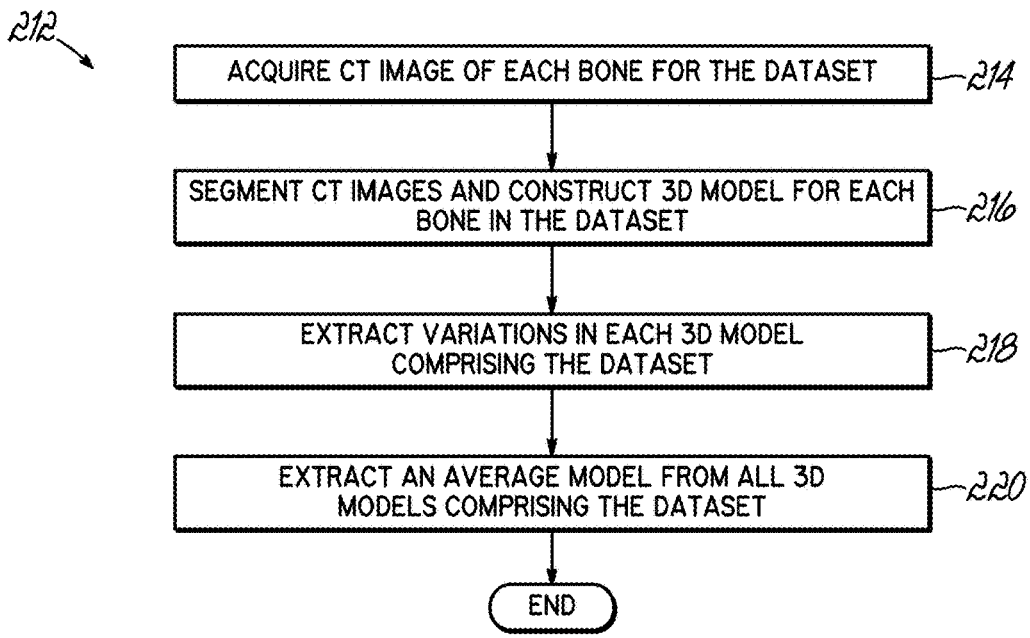
FIG. 25 is a flow chart illustrating one exemplary method of generating a statistical atlas of bone models.

After the point clouds 194 are formed, a bone model may be optimized in accordance with the point clouds 194. That is, the bone point cloud 194 is then used to reconstruct a 3-D patient-specific model of the surface of the scanned bone. The reconstruction begins with a determination of a bone model from which the 3-D patient-specific model is derived (Block 210). The bone model may be a generalized model based on multiple patient bone models and may be selected from a principle component analysis ("PCA") based statistical bone atlas. One such a priori bone atlas, formed in accordance with the method 212 of FIG. 25, includes a dataset of 400 dry bone and tibia bone pairs, scanned by CT (Block 214) and segmented to create models of each bone (Block 216). The method of building and using one such statistical atlas is described in MAHFOUZ M et al., "Automatic Methods for Characterization of Sexual Dimorphism of Adult Femora: Distal Bone," *Computer Methods in Biomechanics and Biomedical Engineering*, 10(6) 2007, which paper is incorporated by reference herein in its entirety.

Each bone model, $M_i$, (where $I \in [1, N]$, N being the number of models in the dataset) has the same number of vertices, wherein the vertex, $V_j$ in a select one model corresponds (at the same anatomical location on the bone) to the vertex, $V_j$, in another one model within the statistical atlas.

PCA was then performed on each model in the dataset to extract the modes of variation of the surface of the bone (Block 218). Each mode of variation is represented by a plurality of eigenvectors resulting from the PCA. The eigenvectors, sometimes called eigenbones, define a vector space of bone morphology variations extracted from the dataset.

The PCA may include any one model from the dataset, expressed as a linear combination of the eigenbones. An average model of all of the 3-D models comprising the dataset is extracted (Block 220) and may be defined as:

$$M_{avg} = \frac{1}{N}\sum_{i=1}^{N} M_i \quad (12)$$

$$M_i = M_{avg} + \sum_{k=1}^{L} \alpha_{ik}U_k \, \forall \, i \in [1, N] \quad (13)$$

Where the variables are defined as follows:

| | |
|---|---|
| $M_{avg}$ | is the mean bone of the dataset |
| L | dimensionality of the eigenspace (i.e., the number of eigenbones) and is equal to N |
| N | number of models in the data |
| $U_k$ | $k^{th}$ eigenbone |
| $\alpha_{ik}$ | $k^{th}$ shape descriptor or eigenbone's coefficient for the $i^{th}$ model |

Furthermore, any new model, $M_{new}$, i.e., a model not already existing in the dataset, may be approximately represented by new values of the shape descriptors (eigenvectors coefficients) as follows:

$$M_{new} \approx M_{avg} + \Sigma_{k=1}^{w}\alpha_k U_k \quad (14)$$

Where the variables are defined as follows:

| | |
|---|---|
| $M_{new}$ | new bone model |
| $\alpha_k$ | indexed shape descriptors for the new model |
| W | number of principal components to use in the model approximation, where W ≤ L |

The accuracy of $M_{new}$ is directly proportional to the number of principal components (W) used in approximating the new model and the number of models, L, of the dataset used for the PCA. The residual error or root mean square error ("RMS") for using the PCA shape descriptors is defined by:

$$RMS = rms[M_{new} - (M_{avg} + \Sigma_{k=1}^{w}\alpha_k U_k)] \quad (15)$$

Therefore, the RMS when comparing any two different models, A and B, having the same number of vertices is defined by:

$$RMS = rms(A-B) = \sqrt{\frac{\sum_{j=1}^{m}\|V_{Aj} - V_{Bj}\|^2}{m}} \quad (16)$$

Where $V_{Aj}$ is the $j^{th}$ vertex in model A, and similarly, $V_{Bj}$ is the $j^{th}$ vertex in model B.

Referring again to the flow chart of method 150 in FIG. 15, the average model ("AVERAGE" branch of Block 210) is loaded (Block 230) or a subset model is selected ("SELECTED" branch of Block 210) from the statistical atlas based on demographics that are similar to the patient and loaded (Block 232) for optimization. The bone point cloud 194 is then applied to the loaded model (Block 234) so that the shape descriptors of the loaded model may be changed to create the 3-D patient-specific model. If desired, one or more shape descriptors may be constrained ("YES" branch of Block 254) so that the 3-D patient-specific model will have the same anatomical characteristics as the loaded model. Accordingly, the one or more shape descriptors are set (Block 238). With the constraints set, the loaded model may be deformed (or optimized) (Block 240) into a model that resembles the appropriate bone and not an irregularly, randomly shaped model. If no constraints are desired ("NO" branch of Block 240) and then the loaded model is optimized (Block 240).

Changing the shape descriptors to optimize the loaded model (Block 240) may be carried out by one or more optimization algorithms. These algorithms may be guided by a scoring function to find the values of the principal components coefficients to create the 3-D patient-specific new model, and are described with reference to FIG. 26. The illustrated optimization algorithm includes a two-step optimization method of successively-applied algorithms to obtain the 3-D patient-specific model that best fits the bone point cloud 194 as discussed below. Although a two-step method is described, the present invention is not limited to a two-step optimization method.

Figure 26:
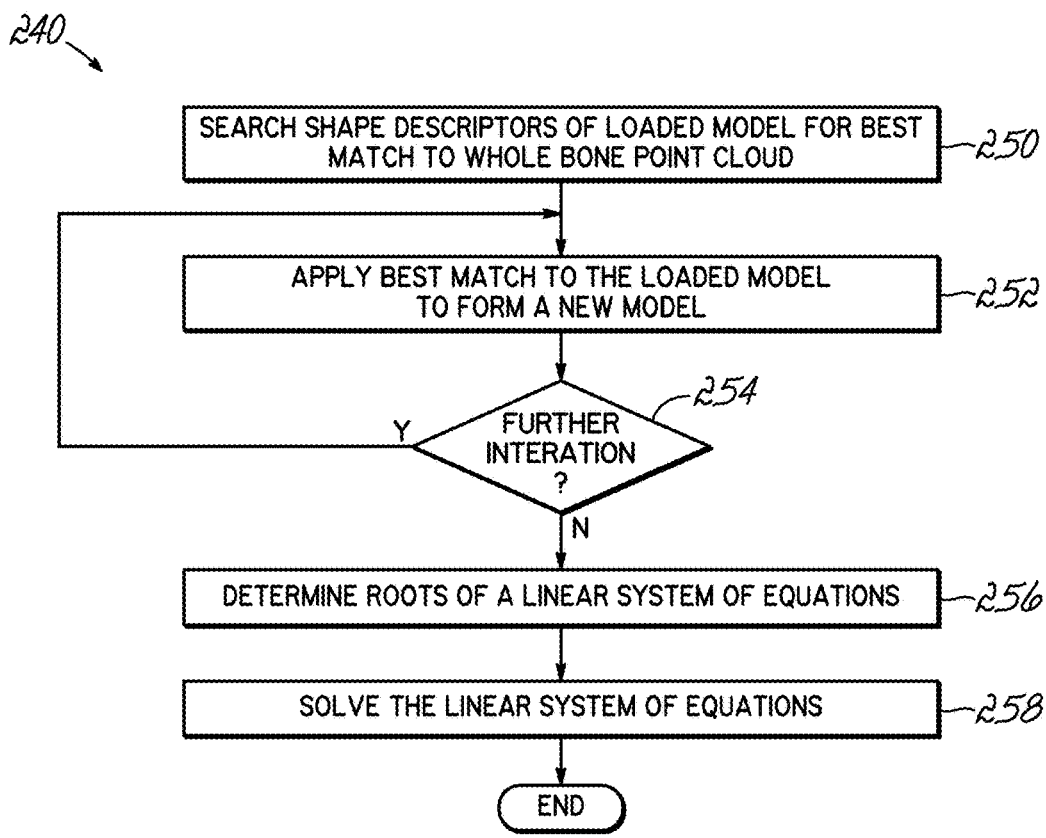
FIG. 26 is a flow chart illustrating one exemplary method of optimizing a bone model to the bone point cloud.

Referring now to FIG. 26, the first algorithm may use a numerical method of searching the eigenspace for optimal shape descriptors. More specifically, the first algorithm may be an iterative method that searches the shape descriptors of the loaded model to find a point that best matches the bone point cloud 194 (Block 250). One such iterative method may include, for example, Powell's conjugate gradient descent method with a RMS as the scoring function. The changes are applied to the shape descriptors of the loaded model by the first algorithm to form a new model, $M_{new}$, (Block 252) defined by Equation 14. The new model, $M_{new}$, is then compared with the bone point cloud 194 and the residual error, E, calculated to determine whether a further iterative search is required (Block 254). More specifically, given a bone point cloud, Q, having n points therein, and an average model, $M_{avg}$, with l vertices, there may be a set of closest vertices, V, in the average model, $M_{avg}$ to the bone point cloud, Q.

$$v_i = \operatorname{argmin}_{v_j \in M}\|v_j - q_i\| \forall i \in [1,n], j \in [1,l] \quad (17)$$

Where $v_i$ is the closest point in the set, V, to $q_i$ in the bone point cloud, Q. An octreemay be used to efficiently search for the closest points in $M_{new}$. The residual error, E, between the new model, $M_{new}$ and the bone point cloud, Q, is then defined as:

$$E = \|V - Q\|^2 \quad (18)$$

With sufficiently high residual error ("YES" branch of Block 254), the method returns to further search the shape descriptors (Block 250). If the residual error is low ("NO" branch of Block 254), then the method proceeds.

The second algorithm of the two-step method refines the new model derived from the first algorithm by transforming the new model into a linear system of equations in the shape descriptors. The linear system is easily solved by linear system equation, implementing conventional solving techniques, which provide the 3-D patient-specific shape descriptors.

Referring again to FIG. 26, and to transform the new model into the linear system, the roots of the linear system must be determined (Block 256). More specifically, the first partial derivatives of the residual error, E, with respect to the shape descriptors, $\alpha_k$, are equal to zero. The error function, Equation 18, may be expressed in terms of the vertices, $v_i$, of the set, V, and the points, $p_i$, of the point cloud, Q:

$$E = \Sigma_{i=1}^{m}\|v_i - q_i\|^2 \quad (19)$$

And may also be expressed in terms of the new model's shape descriptors as:

$$E=\|(V_{avg}+\Sigma_{k=1}^{w}\alpha_k U'_k)-Q\|^2 \quad (20)$$

Where $V_{avg}$ is the set of vertices from the loaded model's vertices, which corresponds to the vertices set, V, that contains the closest vertices in the new model, $M_{new}$, that is being morphed to fit the bone point cloud, Q. $U'_k$ is a reduced version of the $k^{th}$ eigenbone, $U_k$, containing only the set of vertices corresponding to the vertices set, V.

Combining Equations 19 and 20, E maybe expressed as:

$$E=\Sigma_{i=1}^{m}\|(v_{avg,i}+\Sigma_{k=1}^{w}\alpha_k u'_{k,i})-q_i\|^2 \quad (21)$$

Where $v_{avg,i}$ is the $i^{th}$ vertex of $V_{avg}$. Similarly, $u'_{k,i}$ is the $i^{th}$ vertex of the reduced eigenbone, $U'_k$.

The error function may be expanded as:

$$E=\Sigma_{i=1}^{m}[(x_{avg,i}+\Sigma_{l=1}^{w}\alpha_l x_{u',l,i}-x_{q,i})^2+(y_{avg,i}+\Sigma_{l=1}^{w}\alpha_l y_{u',l,i}-y_{q,i})^2+(z_{avg,i}+\Sigma_{l=1}^{w}\alpha_l z_{u',l,i}-z_{q,i})^2] \quad (22)$$

Where $x_{avg,i}$ is the x-coordinate of the $i^{th}$ vertex of the average model, $x_{k,i}$ is the x-coordinate of the $i^{th}$ vertex of the $k^{th}$ eigenbone, and $x_{Q,i}$ is the x-coordinate of the $i^{th}$ point of the point cloud, Q. Similar arguments are applied to the y- and z-coordinates. Calculating the partial derivative of E with respect to each shape descriptor, $\alpha_k$, yields:

$$\frac{\partial E}{\partial \alpha_k}=0 \;\forall\, k \in [1, W] \quad (23)$$

$$\frac{\partial E}{\partial \alpha_k}= \quad (24)$$

$$\sum_{i=1}^{m}\left[2\left(x_{avg,i}+\sum_{l=1}^{w}a_l x_{u',l,i}-x_{p,i}\right)x_{k,i}+2\left(y_{avg,i}+\sum_{l=1}^{w}a_l y_{u',l,i}-y_{p,i}\right)y_{k,i}+2\left(z_{avg,i}+\sum_{l=1}^{w}a_k z_{u',l,i}-z_{p,i}\right)z_{k,i}\right]=0 \;\forall\, k \in [1, W]$$

Recombining the coordinate values into vectors yields:

$$\frac{\partial E}{\partial \alpha_k}=\sum_{i=1}^{m}\left[(v_{avg,i}\cdot u'_{k,i})+\left(\sum_{l=1}^{w}a_l u'_{l,i}\right)\cdot u'_{k,i}-q_i\cdot u'_{k,i}\right]=0 \;\forall\, k \in [1, W] \quad (25)$$

And with rearrangement:

$$\Sigma_{i=1}^{m}(\Sigma_{l=1}^{w}\alpha_l(u'_{l,i}\cdot u'_{k,i}))=\Sigma_{i=1}^{m}[q_i\cdot u'_{k,i}-(v_{avg,i}\cdot u'_{k,i})] \quad (26)$$

Reformulating Equation 26 into a matrix form provides a linear system of equations in the form of Ax=B:

$$\sum_{i=1}^{m}\begin{bmatrix} u'_{1,i}\cdot u'_{1,i} & u'_{2,i}\cdot u'_{1,i} & \cdots & \cdots & u'_{W,i}\cdot u'_{1,i} \\ u'_{1,i}\cdot u'_{2,i} & u'_{2,i}\cdot u'_{2,i} & \cdots & \cdots & u'_{W,i}\cdot u'_{2,i} \\ \vdots & \vdots & \ddots & \ddots & \vdots \\ \vdots & \vdots & \ddots & \ddots & \vdots \\ u'_{1,i}\cdot u'_{W,i} & u'_{2,i}\cdot u'_{W,i} & \cdots & \cdots & u'_{W,i}\cdot u'_{W,i} \end{bmatrix}\begin{bmatrix} a_1 \\ a_2 \\ \vdots \\ \vdots \\ a_W \end{bmatrix}= \quad (27)$$

$$\sum_{i=1}^{m}\begin{bmatrix} (q_i-v_{avg,i})\cdot u'_{1,i} \\ (q_i-v_{avg,i})\cdot u'_{2,i} \\ \vdots \\ \vdots \\ (q_i-v_{avg,i})\cdot u'_{W,i} \end{bmatrix}$$

The linear system of equations may be solved using any number of known methods, such as singular value decomposition (Block 258).

In one embodiment, the mahalanobis distance is omitted because the bone point clouds are dense, thus providing a constraining force on the model deformation. Therefore the constraining function of the mahalanobis distance may not be needed, but rather is avoided to provide the model deformation with more freedom to generate a new model that best fit the bone point cloud.

An ultrasound procedure in accordance with the embodiments of the present invention may, for example, generate approximately 5000 ultrasound images. The generated 3-D patient-specific models (Block 260, FIG. 15), when compared against CT-based segmented models, yielded an average error of approximately 2 mm.

The solution to the linear set of equations provides a description of the patient-specific 3-D model derived from an average, or select, model from the statistical atlas. This 3-D model may be optimized in accordance with the point cloud transformed from a bone contour that was isolated from a plurality of RF signals. The solution may be applied to the average model to display a patient-specific 3-D bone model for aiding in pre-operative planning, mapping out injection points, planning a physical therapy regiment, or other diagnostic and/or treatment-based procedures that involves a portion of the musculoskeletal system.

Cartilage 3-D models may be reconstructed a method that is similar to that which was outlined above for bone. During contour extraction, the contour of the cartilage is more difficult to detect than bone. Probabilistic modeling (Block 171) (FIG. 18) is used to process the raw RF signal to more easily identify cartilage, and SVM aids in detection of cartilage boundaries (Block 173) based on MRI training sets. A cartilage statistical atlas is formed by a method that may be similar to what was described for bone; however, as indicated previously, MRI is used rather than the CT (which was the case for bone). The segmentation (Block 216) (FIG. 25), variation extraction (Block 218) and base model morphing (Block 240) (FIG. 15) are processed to produce a reconstructed cartilage model in the same manner as a bone model is reconstructed. The cartilage model may be displayed alone, or in conjunction with the 3D patient-specific bone model.

Figure 27:
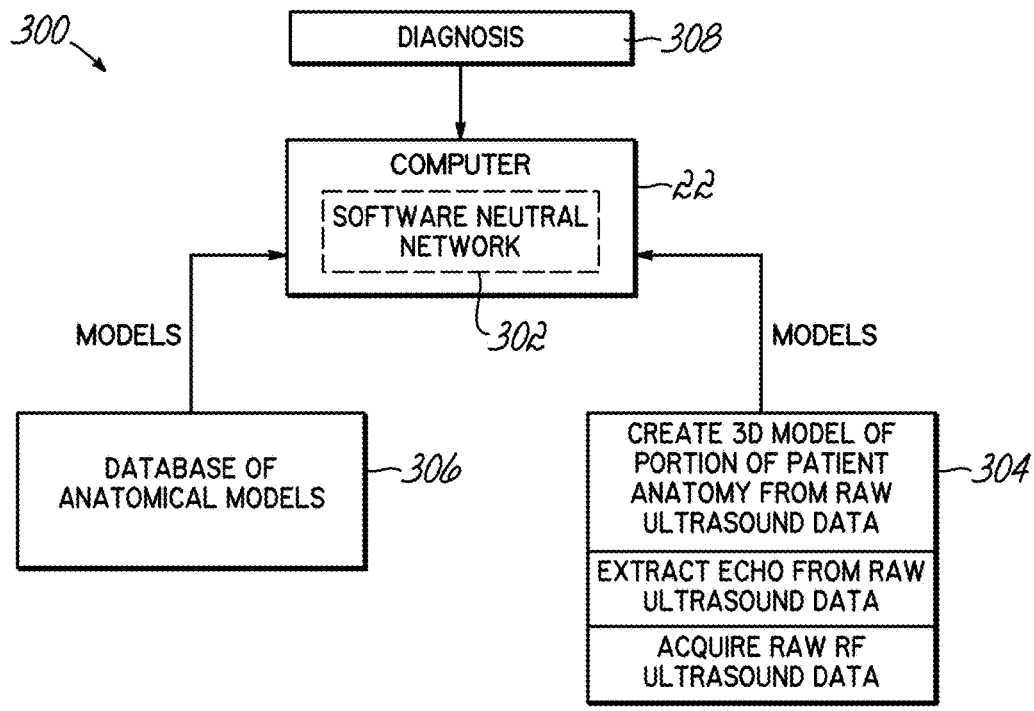
FIG. 27 is a schematic diagram of a diagnostic system which compares 3-D model generated from ultrasound data to a database of anatomical models using a neural network in accordance with one embodiment of the present invention.

Referring now to FIG. 27, a diagnostic system 300 includes a software based neural network 302, which may be in the form of program code 50 residing in the memory 42 of computer 22. A first module 304 may output a 3-D model of a portion of the patient's anatomy to the computer 22 for data processing by way of the neural network 302. A second module 306 may include a database of anatomical datasets (e.g., the orthopedic-specific data set 23) or models, and may output one or more of these models to the computer 22 for processing by the neural network 302. That is, the 3-D model may be compared to the database of models by the neural network 302. The neural network 302 may then return a diagnosis based on the comparison. The information provided also allows the visualization of air where it should not exist, such as in portions of the abdomen, and also fluid in the chest. These may be important areas or diagnosis for an injured patient. The data processing may provide one or more of a visual output, an audible output, and a diagnosis by way of a suitable visual display 308, such as the monitor 26.

Figure 28:
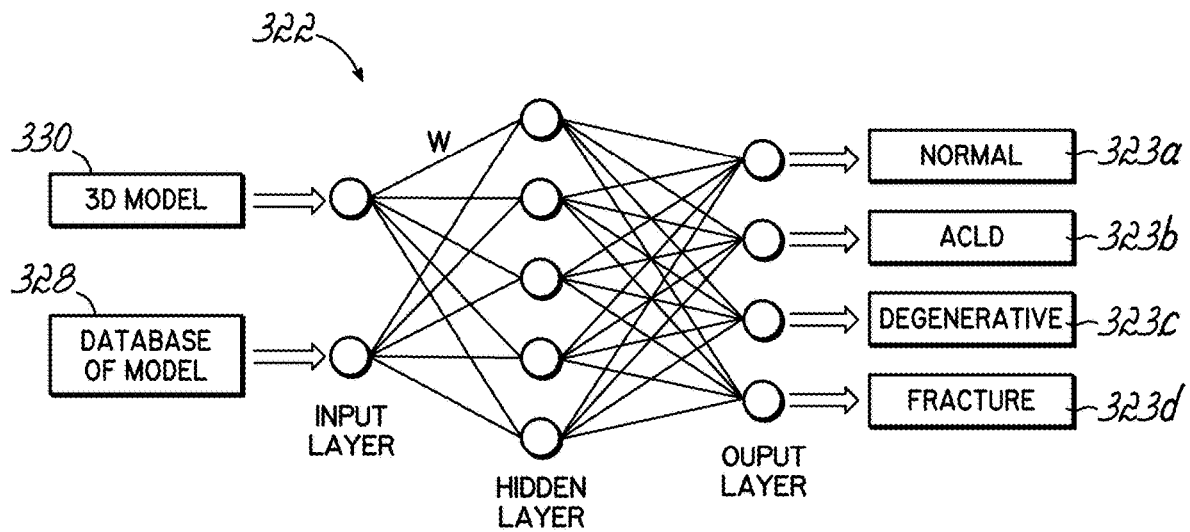
FIG. 28 is a diagrammatic representation of a neural network classifier in accordance with one embodiment of the present invention.

FIG. 28 illustrates one embodiment of a neural network classifier 322 having multiple binary outputs 323*a*, 323*b*, 323*c*, 323*d*, i.e., each output is either a "1" or "0," wherein the "1" corresponds to "yes" and the "0" corresponds to "no." In this neural network classifier 322, each output 323a, 323b, 323c, 323d represents the response of the neural network 302 to a particular condition or injury type. For example, one output 323a may represent a normal or uninjured condition, while another output 323b may represent the response for anterior cruciate ligament deficit or some other trauma. In either case, the output state of the respective condition will be "1" if the state is detected, and "0" otherwise. Similarly, the neural network 302 may output an appropriate state for other diagnosed conditions, such as a degenerative condition 323c or a fracture 323d. The neural network 302 and the classifier 322 may be significantly more or less sophisticated, depending on the underlying model of the anatomical feature in question.

Figure 29:
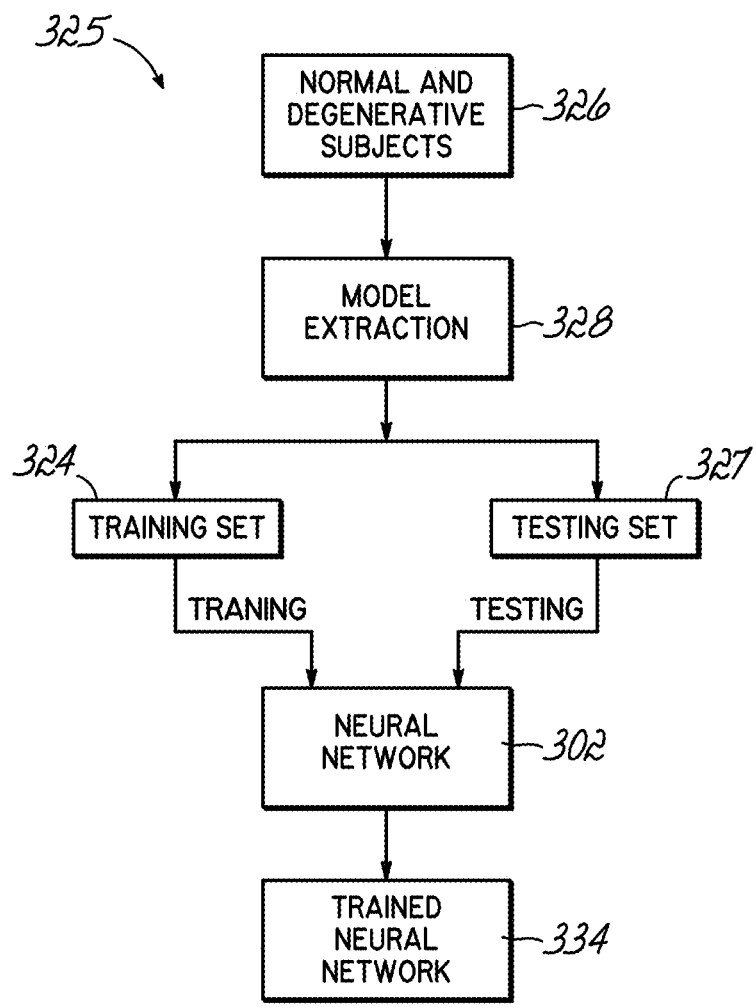
FIG. 29 is a diagrammatic representation of a construction of a neural network.

FIG. 29 illustrates one embodiment of a construction 325 of the neural network 302. The construction 325 includes formulating a supervised classifier using a training set 324 of the database of anatomical models to a dataset 326 of normal and injured anatomical models. The neural network 302 is trained with the training set 324 of vectors, wherein each vector consists of data (e.g., 3-D ultrasound models) collected from one or more patients 10 or test subjects.

Once the neural network 302 is trained, the neural network 302 may be used to classify new cases and categorize an injury type using raw ultrasound data. Those skilled in the art will readily understand that the types and classifications desired to be accommodated by the neural network 302 necessarily include training the neural network 302 on these very types of classifications. Exemplary types and classifications of injuries to mammalian anatomy include, without limitation, trauma conditions, soft tissue damage, and bone fractures. Likewise, the neural network 302 will need to be trained to differentiate between and normal and abnormal anatomical conditions.

Bony trauma diagnosis of the spine, ribs, and clavicle may be imaged in 3-D for diagnosing fracture and dislocation. The complexity of the thoracic and lumbar spine occludes certain areas, making fractures additionally difficult to locate in an austere environment. The diagnostic algorithm is configured to compare an obtained 3D model to a baseline model to alert the operator to areas of concern, such as where a portion of bone is out of a statistical variance limit with respect to the baseline. 3-D visualization is particularly helpful with the lumbar spine, where complex structures and overlapping facet joints make fracture identification additionally complex. The whole-bone a priori database is used to find the most likely shape of the vertebrae despite portions occluded from the ultrasound field of view. This also allows discontinuities to be detected even in some cases where the site of fracture is outside the ultrasound field of view.

With respect to internal hemorrhage, retroperitoneal bleeding, and hemothorax, a volume imaging mode of the invention uses the gathered data and allows visualization of blood from blunt or perforating trauma where the underlying injury is hidden, as well as mutilating trauma where excessive external tissue damage and bleeding may obscure additional internal trauma. This mode works well even in hypotensive casualties. The location of the fluid collection is easily correlated to associated organ and vascular injury. This knowledge may be particularly important in preventing early death from hemorrhage.

For evaluating pneumothorax, areas of air may be identified in the data. The air can be visualized and differentiated from bone, soft tissue or fluid. Crisp boundaries of black in the pleural space may identify air in the lungs. Artifacts such as lung sliding and comet tail which are typically created during normal breathing efforts are typically absent in the case of pneumothorax. Usually, the preferred view is between the 2nd intercostals space. If pneumothorax is confirmed, needle thoracentesis (thoracostomy) is typically indicated. A follow-up scan can be made by replacing the ultrasound cover front after needle insertion to confirm adequate depth has been achieved (i.e. air evacuated). The identification of GI perforation will be investigated by applying the same techniques to the lower abdominal area, and may be an additional feature identified though the free fluid and air imaging modes.

While the invention has been illustrated by a description of various embodiments, and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicant's general inventive concept.

What is claimed is:

1. A method of examining a patient using ultrasound, the method comprising:
  positioning an ultrasound cover on the patient, the ultrasound cover comprising a body drape having at least two layers, wherein a first layer is configured to conform to a shape of a patient's body, the first layer is comprising a vacuum passage within the first layer and a plurality of apertures coupled to the vacuum passage, and
  a plurality of ultrasound sensors positioned within the first layer;
  acquiring raw RF ultrasound signals from at least one of the plurality of ultrasound sensors;
  extracting a plurality of echoes directly from the raw RF ultrasound signals; and
  creating a 3-D model of a portion of the patient'body using at least one echo from the plurality of echoes extracted directly from the raw RF ultrasound signals.

2. The method of claim 1 wherein the at least one echo corresponds to a bone contour, a cartilage contour, an air pocket contour, a fluid cavity contour, or a soft tissue contour.

3. The method of claim 1 further comprising:
  comparing, with a neural network or a statistical technique, the 3-D model with a database of models; and
  returning a diagnosis based on the comparison.

4. The method of claim 1 further comprising: performing B-mode ultrasound scan; and
  displaying the 3-D model overlaid with a 2-D image slice in real time as the B-mode ultrasound scan is performed.

5. The method of claim 1 further comprising:
  applying a vacuum to the vacuum passage so that the first layer conforms to the shape.

6. The method of claim 1 wherein the ultrasound cover includes a dynamic sensor that includes a mobile sensor and a track within the first layer, the method further comprising:
  moving the mobile sensor along the track.

7. An ultrasound diagnostic system comprising:
  an ultrasound cover comprising a body drape having at least two layers wherein a first layer is configured to conform to a shape of a patient's body, the first layer further comprising a vacuum passage within the first layer and a plurality of apertures coupled to the vacuum passage, and a plurality of ultrasound sensors positioned within the first layer; and a computer having access to an orthopedic-specific dataset that includes data relating to a plurality of patient bones that statistically models a morphology of a bone, the computer configured to acquire raw RF ultrasound data-signals and to locate bony boundaries by comparing the raw RF ultrasound signals to the orthopedic-specific dataset.

8. The ultrasound diagnostic system of claim 7 wherein the ultrasound cover further comprises:

a membrane removably coupled to the first layer and configured to conform the first layer to the shape.

9. The ultrasound diagnostic system of claim 7 wherein the plurality of ultrasound sensors are positioned within the first layer so that a first portion of the ultrasound cover has a first sensor density, and a second portion of the ultrasound cover has a second sensor density different than the first sensor density.

10. The method of claim 1, further comprising: automatically generating bone contours from the plurality of echoes extracted; generating a bone point cloud using the generated bone contours;

wherein creating the 3-D model comprises creating a 3-D bone model from the bone point cloud.

* * * * *